United States Patent
Pepe et al.

(10) Patent No.: US 10,980,781 B2
(45) Date of Patent: Apr. 20, 2021

(54) 6-AMINO-2,4-DIHYDROPYRANO [2,3-C] PYRAZOLES AND METHODS OF USE

(71) Applicant: Purdue Research Foundation, West Lafayette, IN (US)

(72) Inventors: Antonella Pepe, West Lafayette, IN (US); Andrew Mesecar, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/493,978

(22) PCT Filed: Mar. 29, 2018

(86) PCT No.: PCT/US2018/024992
§ 371 (c)(1),
(2) Date: Sep. 13, 2019

(87) PCT Pub. No.: WO2018/183587
PCT Pub. Date: Oct. 4, 2018

(65) Prior Publication Data
US 2020/0078336 A1    Mar. 12, 2020

Related U.S. Application Data

(60) Provisional application No. 62/478,068, filed on Mar. 29, 2017.

(51) Int. Cl.
*A61K 31/4162* (2006.01)
*A61K 45/06* (2006.01)
*C07D 491/052* (2006.01)

(52) U.S. Cl.
CPC .......... *A61K 31/4162* (2013.01); *A61K 45/06* (2013.01); *C07D 491/052* (2013.01)

(58) Field of Classification Search
CPC ........................ C07D 491/052; A61K 31/4162
See application file for complete search history.

(56) References Cited

U.S. PATENT DOCUMENTS

| | | | |
|---|---|---|---|
| 8,642,660 B2 * | 2/2014 | Goldfarb | A61K 31/47 514/641 |
| 2011/0077250 A1 * | 3/2011 | Ryder | A61K 31/7052 514/236.8 |
| 2011/0275609 A1 | 11/2011 | Luo | |
| 2012/0214824 A1 | 8/2012 | Tait et al. | |

OTHER PUBLICATIONS

Patani et al. (Chem. Rev. 1996, 3147-3176).*
67704-02_2018_07_19_PCTUS1824992_ISRWO.
Turnbull, et al, "Molecular basis of USP7 inhibition by selective small-molecule inhibitors", Nature (2017).
Kategaya, et al, "USP7 small-molecule inhibitors interfere with ubiquitin binding" Nature (2017).

* cited by examiner

*Primary Examiner* — Kamal A Saeed
(74) *Attorney, Agent, or Firm* — Purdue Research Foundation; Liang Zeng Yan

(57) ABSTRACT

The present invention generally relates to 6-amino-2,4-dihydropyrano [2,3-c] pyrazoles as a ubiquitin specific protease 7(USP7) inhibitor useful for the treatment of diseases mediated by malfunction of USP7, such as inflammation, cancer, and immunological disorders. The invention described herein also pertains to pharmaceutical compositions and methods for treating diseases mediated by malfunction of USP7, in mammals using compounds disclosed herein.

16 Claims, No Drawings

6-AMINO-2,4-DIHYDROPYRANO [2,3-C] PYRAZOLES AND METHODS OF USE

CROSS REFERENCE TO RELATED APPLICATIONS

This present patent application is a national stage entry under 35 U.S.C. § 371(b) of International Application No. PCT/US18/24992, filed on Mar. 29, 2018, which relates to and claims the priority benefit of U.S. Provisional Application Ser. No. 62/478,068, filed Mar. 29, 2017, the contents of which are hereby incorporated herein by reference in their entirety.

GOVERNMENT RIGHTS

This invention was made with government support under CA023168 awarded by the National Institutes of Health. The government has certain rights in the invention.

TECHNICAL FIELD

The present disclosure generally relates to novel compounds as a ubiquitin specific protease 7 (USP7) inhibitor useful for the treatment of diseases mediated by USP7 malfunction, such as inflammation, cancer and immunological disorders, and in particular to 6-amino-2,4-dihydropyrano [2,3-c] pyrazoles and methods of use. The invention described herein also pertains to pharmaceutical compositions and methods for treating diseases mediated by malfunction of USP7, in mammals using compounds disclosed herein.

BACKGROUND

This section introduces aspects that may help facilitate a better understanding of the disclosure. Accordingly, these statements are to be read in this light and are not to be understood as admissions about what is or is not prior art.

Ubiquitin (Ub) is a highly conserved 76-amino acid protein that is covalently attached through the formation of an isopeptide bond between the ε-amino of a lysine residues of a protein substrate and the C-terminus of ubiquitin. The conjugation of ubiquitin to protein substrates commonly signals for proteosomal degradation.

Ubiquitin-mediated degradation of regulatory proteins plays a crucial role in numerous cellular processes, including cell-cycle progression, apoptosis, epigenetics and transcriptional regulation. Aberrations of ubiquitin-mediated processes have been linked to pathological conditions, including cancer, inflammation, and immunological diseases. While the attachment of ubiquitin to substrate proteins is catalyzed by the sequential action of E1, E2 and E3 enzymes, the cleavage of ubiquitin is facilitated by specialized proteases called deubiquitinases (DUBs). The most studied of the DUBs is USP7, which has been shown to play an important role in cancer through the regulation of the activity and cellular levels of tumor suppressor proteins such as p53, PTEN, and FOXO4.

The existence of a dynamic and complex interplay between p53 and its regulatory proteins Mdm2 (corresponding to Hdm2 in humans, however we will continue referring to Mdm2 for simplicity) and USP7 has been demonstrated in several studies (Cummins, J. M. et al. *Nature* 2004, 428, 6982). While the specifics of this interaction are still unclear, it is generally understood that in normal conditions cellular levels of p53 are very low, due to its rapid proteosomal degradation, induced by the Mdm2-catalyzed ubiquitination. USP7 participates in maintaining a dynamic equilibrium through its ability to deubiquitinate Mdm2 and p53.

While both proteins compete for the same binding site on USP7, in the N-terminal TRAF-like domain, under normal, unstressed cellular conditions Mdm2 is the preferred substrate for USP7. Upon DNA damage and in stressed cells, ATP-dependent phosphorylation of Mdm2 lowers its affinity for USP7, resulting in a stress-induced degradation of Mdm2. In these condition USP7 preferentially deubiquitinates p53, resulting in an overall stabilization of p53. (Zilfou, J. T. et al. *Cold Spring Harbor Perspectives in Biology* 2009, 1 (5), a001883).

RNA interference studies have shown that USP7 silencing reduces cells proliferation through induction of apoptosis. This phenotype was observed only in cancer cell lines with wild-type p53, including HCT116, MCF-7 and A549, and was associated with increased cellular levels of p53 and increased degradation of Mdm2.

USP7 is also involved in processes of cellular proliferation that are independent from p53. A representative example is the interaction with transcription factors of the fork head box O (FOXO) family. Recent studies have shown that following oxidative stress, FOXO4 undergoes ubiquitination, and consequent translocation to the nucleus and activation. The deubiquitynating activity of USP7 negatively affects FOXO4 localization to the nucleus and transcriptional activity (van der Horst, A. et. al. *Nat. Cell. Biol.* 2006, 8 (10), 1064-1073).

Similarly, nuclear localization of the phosphatase and tensin homologue (PTEN) is crucial for its role as a tumor suppressor protein. Mono ubiquitination induces translocation of PTEN to the nucleus and the reverse reaction, catalyzed by USP7, causes its nuclear exclusion, blocking its apoptotic potential in prostate cancer cells (Song, M. S. et. al. *Nature* 2008, 455 (7214), 813-817).

Overexpression of USP7 has been shown to correlate with tumor aggressiveness in several cancers (including prostate, non-small cell lung cancer and glioma) and with short patient survival time and high malignancy in non-small cell lung cancers. Taken together, the results of USP7 silencing experiments and the data showing the crucial involvement of USP7 in oncogenic pathways suggest that small molecule inhibitors of USP7 have potential for anticancer therapies.

The FDA approval of the proteasome inhibitor Bortezomib has validated the approach of targeting protein degradation pathways and has also driven the development of small molecules targeting related enzymes. One of the limitations of Bortezomib therapy is the development of resistance, which limits its long-term utility. Small molecules inhibiting USP7 may overcome this resistance and indeed have showed to induce apoptosis in multiple myeloma cells resistant to bortezomib. Inhibitors of USP7 have been discovered, but many of them have issues such as selectivity (due to the high homology of proteases, particularly in the catalytic domain) or poor pharmacokinetic properties.

SUMMARY OF THE INVENTION

This present disclosure relates to compounds having a formula (I)

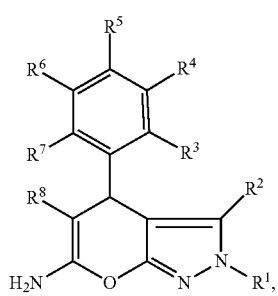

or a pharmaceutically acceptable salt, hydrate, or solvate thereof, wherein
- $R^1$ is hydrogen, an alkyl or an acyl;
- $R^2$ is a heterocyclyl, cycloalkyl, cycloalkenyl, cycloheteroalkyl, cycloheteroalkenyl, aryl, heteroaryl, arylalkyl, arylalkenyl, or arylalkynyl, each of which is optionally substituted;
- $R^3$, $R^4$, $R^5$, $R^6$, and $R^7$ represent five substituents each independently selected from the group consisting of hydrogen, halo, azido, cyano, nitro, hydroxy, amino, thio, and derivatives thereof, and an acyl, alkyl, alkenyl, alkynyl, heteroalkyl, heteroalkenyl, oxyalkyl, heteroalkynyl, a heterocyclyl, cycloalkyl, cycloalkenyl, cycloheteroalkyl, cycloheteroalkenyl, aryl, arylalkyl, arylalkenyl, and arylalkynyl, each of which is optionally substituted; or any two adjacent substituents that are taken together with the attached carbons to form an optionally substituted heterocycle and each of other substituents is defined as above; and
- $R^8$ is cyano or a carboxy ester.

In some preferred embodiments, this invention relates to compounds having a general formula (I) wherein $R^1$ is hydrogen.

In some embodiments, this invention relates to compounds having a formula general (I) wherein $R^2$ is an optionally substituted heterocycle.

In some preferred embodiments, this invention relates to compounds having a formula general (I), wherein $R^2$ is

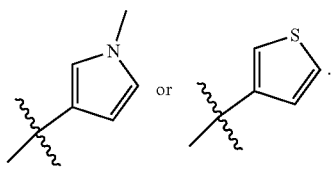

In some preferred embodiments, this invention is related to compounds having a formula general (I) wherein $R^8$ is cyano or a carboxy ester.

In some other embodiments, this invention is related to a pharmaceutical composition comprising one or more compounds disclosed herein, or a pharmaceutically acceptable salt thereof, together with one or more diluents, excipients or carriers.

In some other embodiments, this invention is related to a method for treating diseases mediated by USP7 malfunction, such as inflammation, cancer and immunological disorders, comprising the step of administering a therapeutically effective amount of one or more compounds disclosed herein, and one or more carriers, diluents, or excipients, to a patient in need of relief from said disorder.

In some other embodiments, this invention is related to a method for treating diseases mediated by USP7 malfunction, such as inflammation, cancer and immunological disorders, comprising the step of administering a therapeutically effective amount of one or more compounds disclosed herein in combination with one or more other compounds of the same or different mode of action, and one or more carriers, diluents, or excipients, to a patient in need of relief from said disorder.

These and other features, aspects and advantages of the present invention will become better understood with reference to the following descriptions and claims.

DETAILED DESCRIPTION

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

The present disclosure generally relates to novel compounds as a ubiquitin specific protease 7 (USP7) inhibitor useful for the treatment of diseases mediated by USP7 malfunction, such as inflammation, cancer and immunological disorders, and in particular to 6-amino-2,4-dihydropyrano [2,3-c] pyrazoles and methods of use. The invention described herein also pertains to pharmaceutical compositions and methods for treating diseases mediated by malfunction of USP7, in mammals using compounds disclosed herein.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or range, for example, within 90%, within 95%, 99%, 99.5%, 99.9%, 99.99%, or at least about 99.999% or more of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

The term "substituted" as used herein refers to a functional group in which one or more hydrogen atoms contained therein are replaced by one or more non-hydrogen atoms. The term "functional group" or "substituent" as used herein refers to a group that can be or is substituted onto a molecule. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, azides, hydroxylamines, cyano, nitro groups, N-oxides, hydrazides, and enamines; and other heteroatoms in various other groups.

The term "alkyl" as used herein refers to substituted or unsubstituted straight chain and branched alkyl groups and cycloalkyl groups having from 1 to about 20 carbon atoms ($C_1$-$C_{20}$), 1 to 12 carbons ($C_1$-$C_{12}$), 1 to 8 carbon atoms ($C_1$-$C_8$), or, in some embodiments, from 1 to 6 carbon atoms ($C_1$-$C_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to substituted or unsubstituted straight chain and branched divalent alkenyl and cycloalkenyl groups having from 2 to 20 carbon atoms ($C_2$-$C_{20}$), 2 to 12 carbons ($C_2$-$C_{12}$), 2 to 8 carbon atoms ($C_2$-$C_8$) or, in some embodiments, from 2 to 4 carbon atoms ($C_2$-$C_4$) and at least one carbon-carbon double bond. Examples of straight chain alkenyl groups include those with from 2 to 8 carbon atoms such as —CH═CH—, —CH═CHCH$_2$—, and the like. Examples of branched alkenyl groups include, but are not limited to, —CH═C(CH$_3$)— and the like.

An alkynyl group is the fragment, containing an open point of attachment on a carbon atom that would form if a hydrogen atom bonded to a triply bonded carbon is removed from the molecule of an alkyne. The term "hydroxyalkyl" as used herein refers to alkyl groups as defined herein substituted with at least one hydroxyl (—OH) group.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. In some embodiments, cycloalkyl groups can have 3 to 6 carbon atoms ($C_3$-$C_6$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be monosubstituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to substituted or unsubstituted aromatic and non-aromatic ring compounds containing 3 or more ring members, of which, one or more is a heteroatom such as, but not limited to, B, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms ($C_3$-$C_8$), 3 to 6 carbon atoms ($C_3$-$C_6$) or 6 to 8 carbon atoms ($C_6$-$C_8$).

A heteroaryl ring is an embodiment of a heterocyclyl group. The phrase "heterocyclyl group" includes fused ring species including those that include fused aromatic and non-aromatic groups. Representative heterocyclyl groups include, but are not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclylalkyl groups include, but are not limited to, furan-2-yl methyl, furan-3-yl methyl, pyridine-3-yl methyl, tetrahydrofuran-2-yl methyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, —CF(CH$_3$)$_2$ and the like.

The term "optionally substituted," or "optional substituents," as used herein, means that the groups in question are either unsubstituted or substituted with one or more of the substituents specified. When the groups in question are substituted with more than one substituent, the substituents may be the same or different. When using the terms "independently," "independently are," and "independently selected from" mean that the groups in question may be the same or different. Certain of the herein defined terms may occur more than once in the structure, and upon such occurrence each term shall be defined independently of the other.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

Further, in each of the foregoing and following embodiments, it is to be understood that the formulae include and represent not only all pharmaceutically acceptable salts of the compounds, but also include any and all hydrates and/or solvates of the compound formulae or salts thereof. It is to be appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers, tautomers and geometric isomers, both individually and in any and all possible mixtures. In each of the foregoing and following embodiments, it is also to be understood that the formulae include and represent any and all crystalline forms, partially crystalline forms, and non-crystalline and/or amorphous forms of the compounds.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other nontoxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

Illustrative formats for oral administration include tablets, capsules, elixirs, syrups, and the like. Illustrative routes for parenteral administration include intravenous, intraarterial, intraperitoneal, epidural, intraurethral, intrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, phanrmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 µg/kg to about 1 g/kg. The dosages may be single or divided, and may administered according to a wide variety of protocols, including q.d. (once a day), b.i.d. (twice a day), t.i.d. (three times a day), or even every other day, once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

In addition to the illustrative dosages and dosing protocols described herein, it is to be understood that an effective amount of any one or a mixture of the compounds described herein can be determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The term "patient" includes human and non-human animals such as companion animals (dogs and cats and the like) and livestock animals. Livestock animals are animals raised for food production. The patient to be treated is preferably a mammal, in particular a human being.

In some illustrative embodiments, the invention relates to a compound of formula (I)

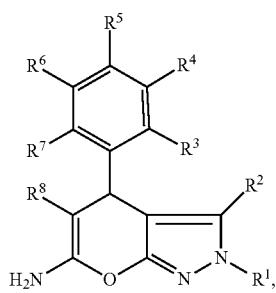

or a pharmaceutically acceptable salt, hydrate, or solvate thereof, wherein
$R^1$ is hydrogen, an alkyl or an acyl;
$R^2$ is a heterocyclyl, cycloalkyl, cycloalkenyl, cycloheteroalkyl, cycloheteroalkenyl, aryl, heteroaryl, arylalkyl, arylalkenyl, or arylalkynyl, each of which is optionally substituted;
$R^3$, $R^4$, $R^5$, $R^6$, and $R^7$ represent five substituents each independently selected from the group consisting of hydrogen, halo, azido, cyano, nitro, hydroxy, amino, thio, and derivatives thereof, and an acyl, alkyl, alkenyl, alkynyl, heteroalkyl, heteroalkenyl, oxyalkyl, heteroalkynyl, a heterocyclyl, cycloalkyl, cycloalkenyl, cycloheteroalkyl, cycloheteroalkenyl, aryl, arylalkyl, arylalkenyl, and arylalkynyl, each of which is optionally substituted; or any two adjacent substituents that are taken together with the attached carbons to form an optionally substituted heterocycle and each of other substituents is defined as above; and
$R^8$ is cyano or a carboxy ester.

In some illustrative embodiments, the invention relates to a compound of formula (I), wherein $R^1$ is hydrogen, an acyl or an alkyl.

In some illustrative embodiments, the invention relates to a compound of formula (I), wherein $R^2$ is an optionally substituted heterocycle.

In some preferred embodiments, the invention relates to a compound of formula (I), wherein $R^2$ is

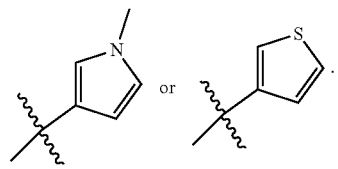

In some illustrative embodiments, the invention relates to a compound of formula (I), wherein $R^1$ is hydrogen, an acyl or an alkyl; and $R^2$ is

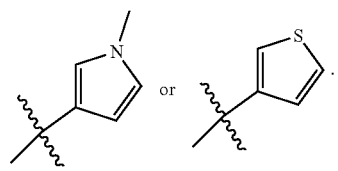

In some illustrative embodiments, the invention relates to a compound of formula (I), wherein $R^4$ or $R^6$ is an alkyl, halo, or haloalkyl.

In some illustrative embodiments, the invention relates to a compound of formula (I), wherein $R^5$ is hydroxyl, amino, nitro, halo, cyano, azido, an alkyl, alkenyl, alkynyl, alkyloxy, alkenyloxy, alkynyl, alkylamino, alkenylamino, oxyalkyl, or alkynylamino.

In some preferred embodiments, the invention relates to a compound of formula (I), wherein $R^5$ is oxyalkyl.

In some illustrative embodiments, the invention relates to a compound of formula (I), wherein $R^5$ is oxyalkyl; and $R^6$ is halo, alkyl, cyano, or haloalky.

In some illustrative embodiments, the invention relates to a compound of formula (I), wherein $R^4$ is hydrogen; $R^5$ is oxyalkyl; and $R^6$ is halo, alkyl, cyano, or haloalky.

In some illustrative embodiments, the invention relates to a compound of formula (I), wherein $R^2$ is an optionally substituted heterocycle; $R^4$ is hydrogen; $R^5$ is oxyalkyl; and $R^6$ is halo, alkyl, cyano, or haloalkyl.

In some illustrative embodiments, the invention relates to a compound of formula (I), wherein $R^1$ and $R^4$ are hydrogen; $R^2$ is an optionally substituted heterocycle; $R^5$ is oxyalkyl; and $R^6$ is halo, alkyl, cyano, or haloalky.

In some illustrative embodiments, the invention relates to a compound of formula (I), wherein $R^4$ or $R^6$ is an alkyl, halo, or haloalkyl, and $R^5$ is an oxyalkyl or aminoalkyl.

In some illustrative embodiments, the invention relates to a compound of formula (I), wherein $R^8$ is a carboxy ester.

In some illustrative embodiments, the invention relates to a compound of formula (I), wherein said compound is

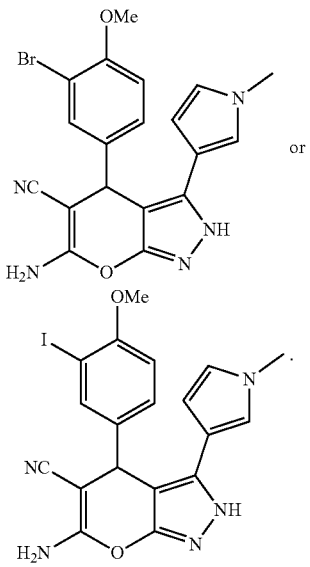

In some illustrative embodiments, the invention relates to a compound of formula (I), wherein said compound is

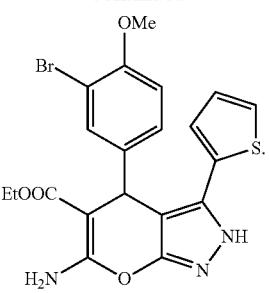

In some illustrative embodiments, the invention relates to a compound of formula (I), wherein said compound is

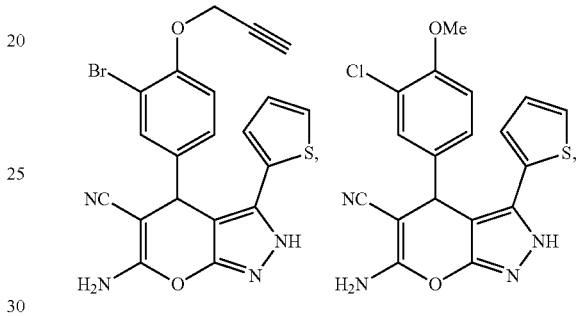

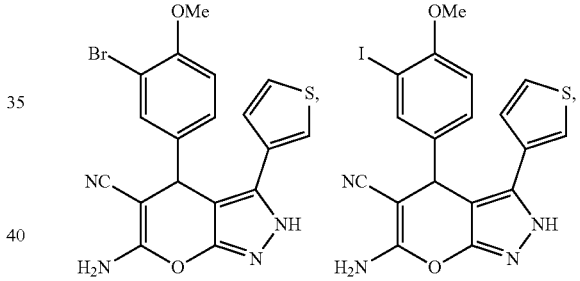

In some illustrative embodiments, the invention relates to a compound of formula (I), wherein said compound is

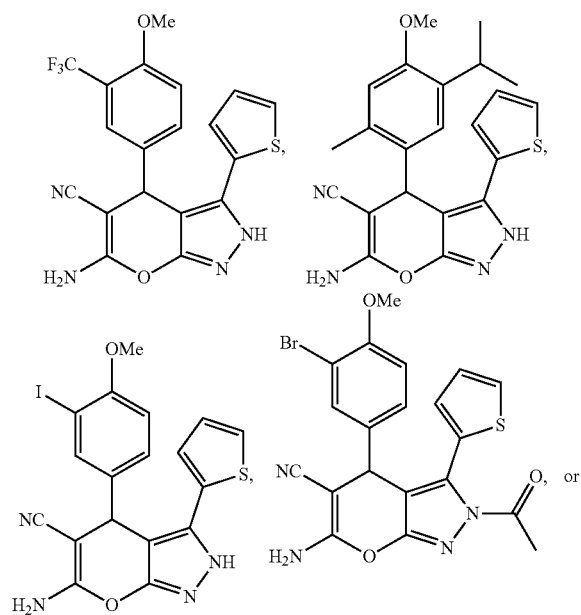

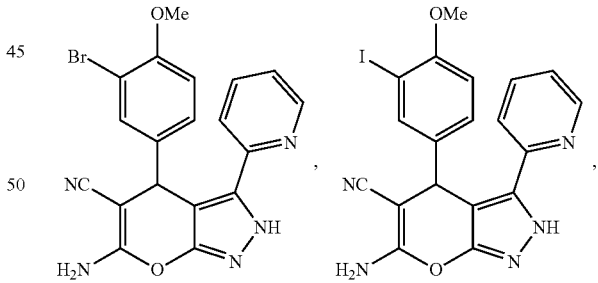

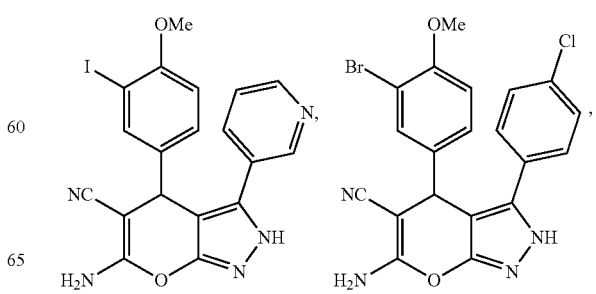

-continued

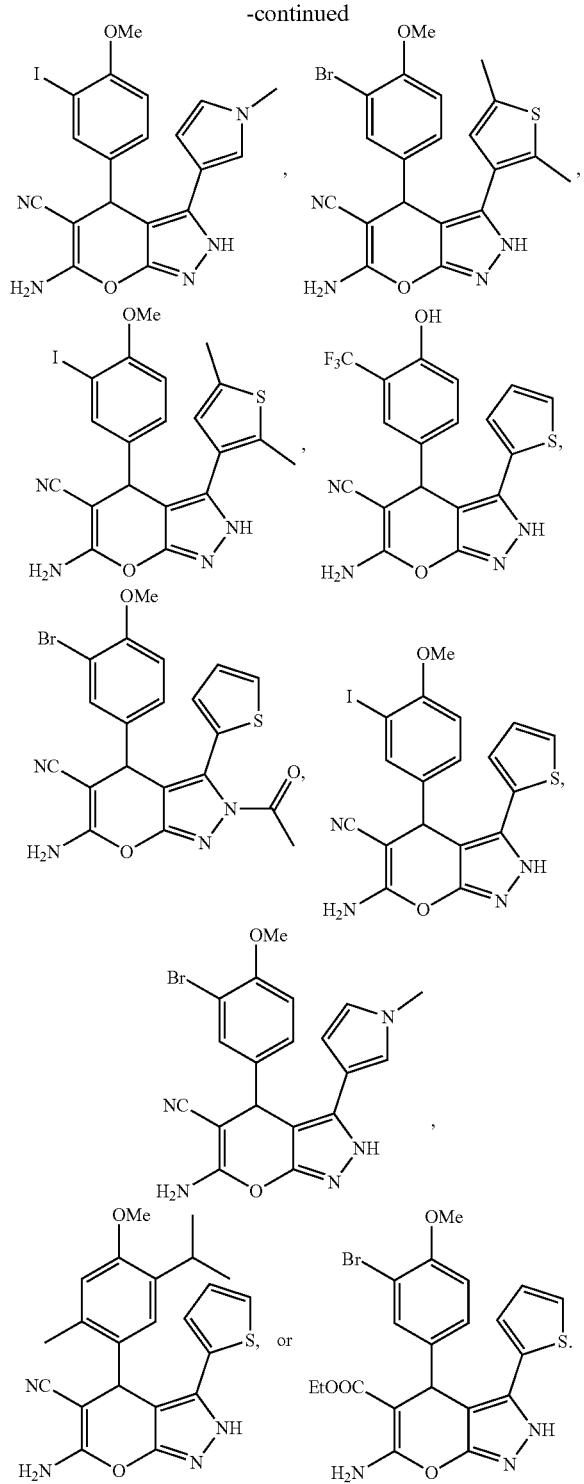

In some other illustrative embodiments, the invention relates to a pharmaceutical composition comprising one or more compounds disclosed herein, or a pharmaceutically acceptable salt thereof, together with one or more diluents, excipients or carriers.

In some other embodiments, this invention is related to a method for treating diseases medicated by USP7 malfunction, such as inflammation, cancer and immunological disorders, wherein the method comprises the step of administering a therapeutically effective amount of one or more compounds disclosed herein, and one or more carriers, diluents, or excipients, to a patient in need of relief from said disorder.

In some other embodiments, this invention is related to a method for treating diseases medicated by USP7 malfunction, such as inflammation, cancer and immunological disorders, wherein the method comprises the step of administering a therapeutically effective amount of one or more compounds disclosed herein in combination with one or more other compounds of the same or different mode of action, and one or more carriers, diluents, or excipients, to a patient in need of relief from said disorder.

In addition, it is appreciated herein that the compounds described herein may be used in combination with other compounds that are administered to treat other symptoms of cancer, such as compounds administered to relieve pain, nausea, vomiting, and the like.

The following non-limiting exemplary embodiments are included herein to further illustrate the invention. These exemplary embodiments are not intended and should not be interpreted to limit the scope of the invention in any way. It is also to be understood that numerous variations of these exemplary embodiments are contemplated herein.

The synthesis began with the reaction of differently substituted methyl ketones 1a-g with diethyl carbonate and NaH in THF to yield aryl substituted β-ketoesters 2a-g (Scheme 1). These were then reacted with hydrazine or methyl hydrazine in refluxing ethanol to generate pyrazolones 4a-h. The regiochemistry of the resulting pyrazolones and the mechanism of the reaction were studied in detail by Katrinsky (Katrizky, A. R., et al., *J. Chem. Soc, Perkin Trans.* 2, 1987, (8), 969) and confirmed by our 2D NMR analysis of the final dihydropyrano [2,3-c] pyrazoles 6a and 9a. The pyrazolones were then used in a three-component reaction with malononitrile or ethylcyanoacetate and differently substituted aldehydes to generate compounds 6a-v, 7a-o and 8 as racemic mixtures (Scheme 2). The three-component reaction was found a convenient method for the preparation of a diverse library of compounds in high purities, and was preferred to the four-component protocol.

The scaffold was further functionalized to investigate the effect of each substituent on the activity (Scheme 3). Alkylation of the amino group at C-6 was obtained in a two steps-protocol which includes first the treatment of compound 6a or 9a with triethyl orthoformate in glacial acetic acid at 110° C. and then the resulting imidate 10 or 12 was reduced to the methyl ethyl ether derivative 11 or to the methyl analogue 13, using respectively 1.5 or 3 equiv. of sodium borohydrate.

Scheme 1: Synthesis of pyrazol-3-ones

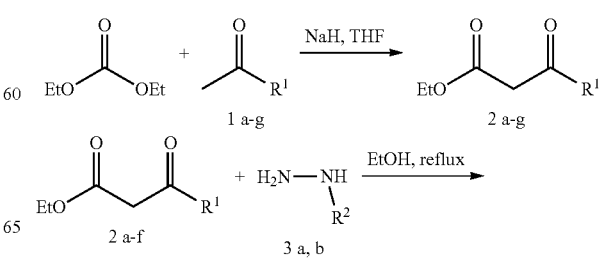

-continued

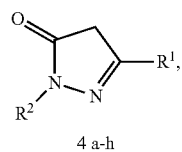

4 a-h

R¹: a = 2-thiophenyl, b = 3-thiophenyl, c = 2-pyridinyl, d = 3-pyridinyl,
e = 4-chlorophenyl, f = 3(N-methyl) pyrrolyl, g = 3-(2,5-dimethylthiophen-3-yl)
3a: R² = H, 3b: R² = Me wherein:

| Compound# | R¹ | R² |
|---|---|---|
| 4a | 2-thiophenyl | H |
| 4b | 3-thiophenyl | H |
| 4c | 2-pyridinyl | H |
| 4d | 3-pyridinyl | H |
| 4e | 4-chlorophenyl | H |
| 4f | 3(N-methyl) pyrrolyl | H |
| 4g | 3-(2,5-dimethylthiophenyl) | H |
| 4h | 2-thiophenyl | Me |

Scheme 2: Synthesis of dihydropyrano [2,3-c] pyrazoles

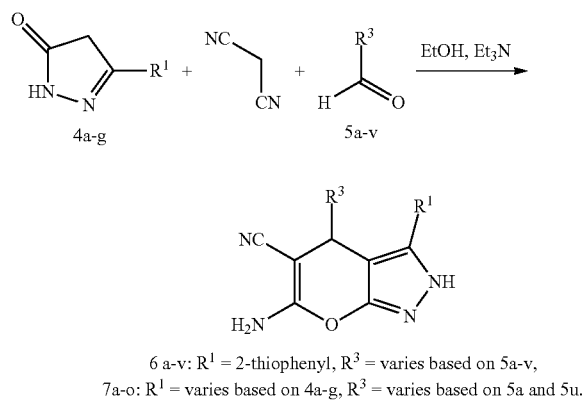

6 a-v: R¹ = 2-thiophenyl, R³ = varies based on 5a-v,
7a-o: R¹ = varies based on 4a-g, R³ = varies based on 5a and 5u.

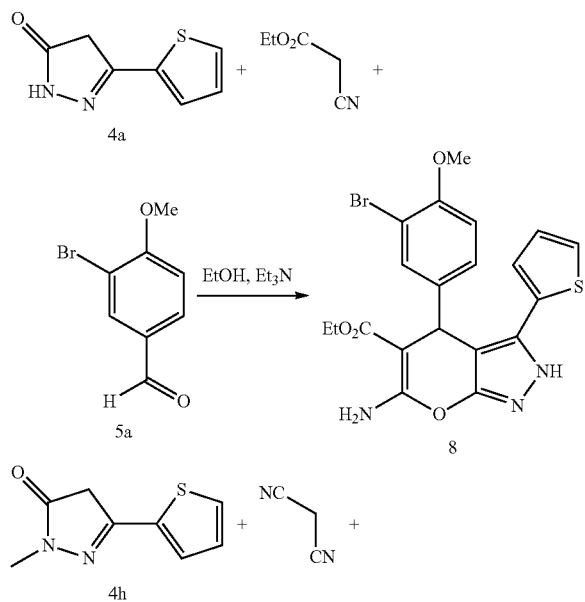

-continued

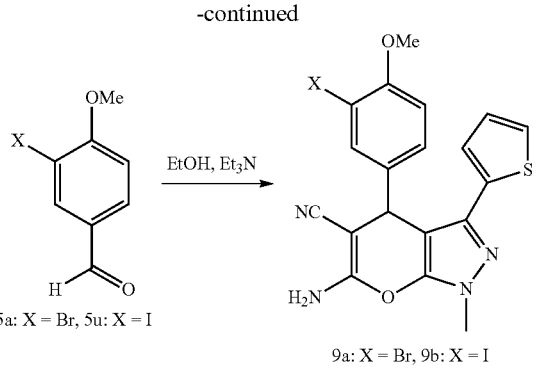

5a: X = Br, 5u: X = I

9a: X = Br, 9b: X = I

Acetylation of 2-N was done by treating compound 6a with acetic anhydride at 110° C. to yield the acetyl derivative 14. Removal of NH₂ occurred in a one-pot reductive deamination protocol, which includes generation of the diazonium salt by reacting compound 6a with tert-butyl nitrite in DMF from −30° C. to room temperature, followed by the reduction of the intermediate with sodium borohydride to yield compound 15 in 31% yield.

Other attempts to modify the scaffold, starting from 6a or 9a were not successful. For example, the hydrolysis of the nitrile (in acidic or basic conditions), or its conversion to the tetrazole (using sodium azide, ammonium chloride and a polar solvent such as DMF or ethanol, at temperatures of 80° C. or 120° C.), resulted in loss of the scaffold or in a retrocondensation, which yielded pyrazolone 4a and arylidene malononitrile.

Scheme 3: Derivatization of dihydropyrano [2,3-c] pyrazoles

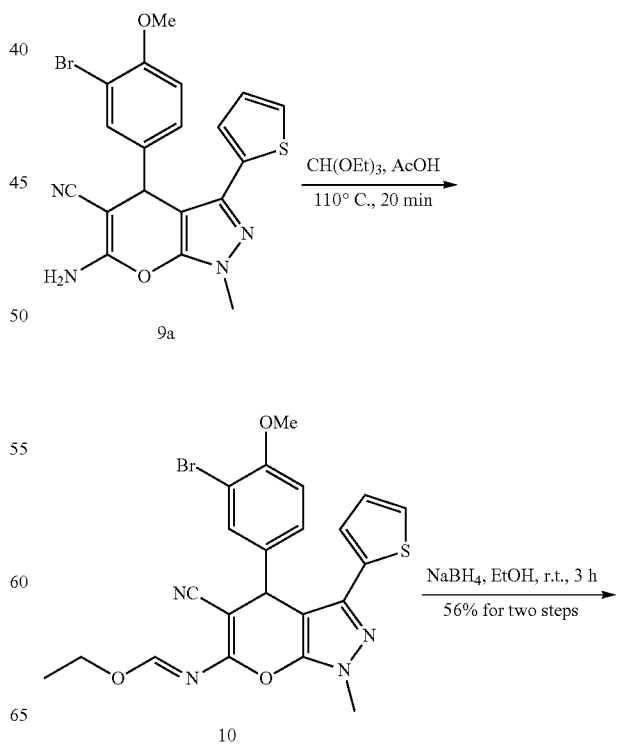

-continued

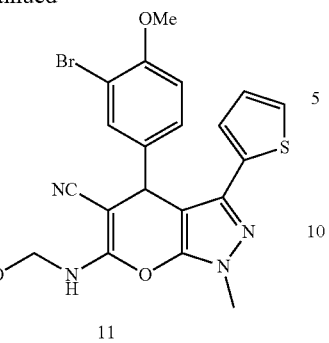

11

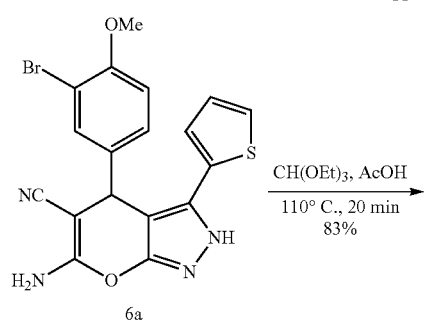

6a

CH(OEt)₃, AcOH
110° C., 20 min
83%
→

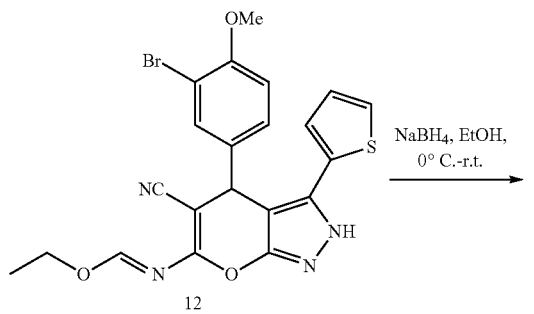

12

NaBH₄, EtOH,
0° C.-r.t.
→

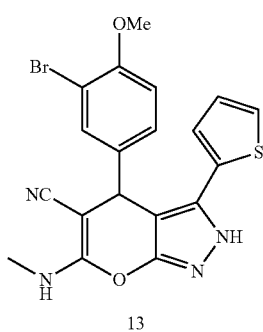

13

Ac₂O, 110° C., 30 min
73%
→

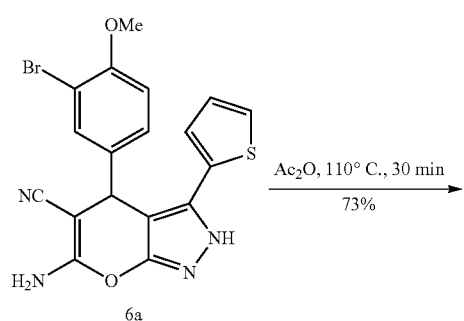

6a

-continued

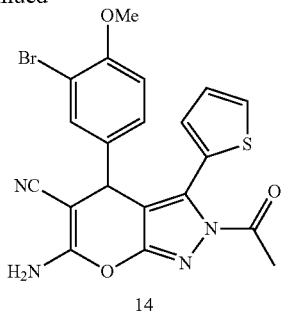

14

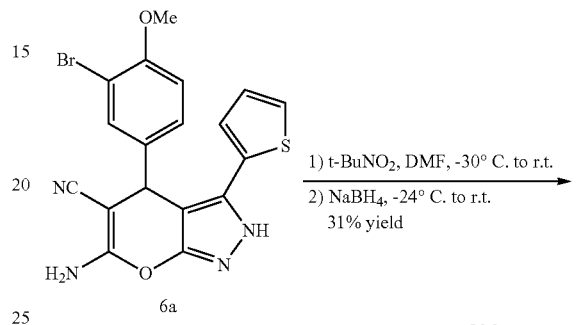

6a 1) t-BuNO₂, DMF, -30° C. to r.t.
2) NaBH₄, -24° C. to r.t.
31% yield
→

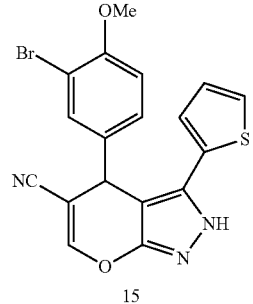

15

Biological Assay and Results

The lyophilized compounds were re-suspended in 100% DMSO to a stock concentration of 10 mM and stored at −20° C. Where Rate$_{sample}$ is the initial slope of the progress curve as measured in Arbitrary Fluorescence Units per second of USP7 in the presence of compound. Rate$_{pos}$ is the initial slope of USP7 without a compound present and Rate$_{neg}$ is the baseline of substrate hydrolysis without USP7 present.

The percent inhibition of USP7 at 100 μM of each compound was determined prior to the determination of IC$_{50}$ values. The final concentration of substrate was held constant at 200 nM and USP7 was held constant at a final concentration of 1 nM in Assay Buffer (50 mM Tris pH 7.5, 5 mM DTT, 0.1 mg/mL BSA, and 0.01% Triton X-100). From the 10 mM stock, each compound to be tested was diluted to a working concentration of 3 mM in 100% DMSO. The assay was performed as follows: 1 μL of the working stock of compound was added to a Costar 96 half-volume black plate to which 15 μL of USP7 was added. Plates were gently mixed and incubated at room temperature for five minutes. To initiate the reaction, 15 μL of Ub-Rho 110 was added. Each assay was measured in triplicate. A negative control of Ub-Rho 110 alone was measured to evaluate the background rate. Control reactions of USP7 without compound (DMSO only) were included to measure the rate of the uninhibited USP7 reaction. All reactions contained a final concentration of 3% DMSO. The reaction progress was measured as a filter based assay in 10-second intervals for a total of 30 minutes at an excitation wavelength of 485 nm and an emission wavelength of 528 nm. The percent inhibition was calculated using Equation (1).

$$\% \text{ Inhibition} = \left[1 - \frac{Rate_{sample} - Rate_{neg}}{Rate_{pos} - Rate_{neg}}\right] \quad \text{(Equation 1)}$$

$$\% \text{ Inhibition} = \frac{\text{Maximum \% Inhibition} * [\text{Inhibitor}]}{[\text{Inhibitor}] + IC_{50}} \quad \text{(Equation 2)}$$

The biochemical activity of the compounds synthesized is reported in Table 1 as a measure of their maximum % inhibition at concentration of 100 μM. $IC_{50}$ values were determined for the compounds that showed a percent inhibition ≥40% at 100 μM. The $IC_{50}$ values were determined with 11 compound concentrations ranging from 6 mM to 5.8 μM in two-fold serial dilutions in 100% DMSO. The assay design was identical to as described above. The percent inhibition was calculated using Equation 1 and fit to Equation 2 by use of the Enzyme Kinetics Module of Sigma Plot (v13:Systat Software Inc.), to determine the $IC_{50}$ value.

TABLE 1

Inhibition of USP7 with compounds disclosed herein.

| Entry | Compound No. | % inhibition @100 μM | $IC_{50}$ (μM) | Entry | Compound No. | % inhibition @100 μM | $IC_{50}$ (μM) |
|---|---|---|---|---|---|---|---|
| 1 | 6a | 72 ± 3 | 3.7 ± 0.4 | 2 | 6b | 10 ± 7 | NA |
| 3 | 6c | 0 | NA | 4 | 6d | 0 | NA |
| 5 | 6e | 0 | NA | 6 | 6f | 31 ± 6 | NA |
| 7 | 6g | 57 ± 2 | 33 ± 5 | 8 | 6h | 38 ± 6 | NA |
| 9 | 6i | 63 ± 1 | NA | 10 | 6l | 26 ± 3 | NA |
| 11 | 6m | 32 ± 5 | NA | 12 | 6n | 84 ± 2 | 4.5 ± 0.6 |
| 13 | 6o | 45 ± 9 | 13 ± 3 | 14 | 6p | 62 ± 20 | NA |
| 15 | 6q | 92 ± 2 | 11.0 ± 0.7 | 16 | 6r | 95 ± 4 | 1.4 ± 0.2 |
| 17 | 6s | 32 ± 13 | 7 ± 2 | 18 | 6t | 55 ± 3 | 7 ± 2 |
| 19 | 6u | 85 ± 1 | 1.8 ± 0.1 | 20 | 6v | 93 ± 4 | 0.75 ± 0.06 |
| 21 | 7a | 72 ± 4 | 8.1 ± 1 | 22 | 7b | 71 ± 3 | 5.6 ± 0.7 |
| 23 | 7c | 85 ± 2 | 7.9 ± 0.4 | 24 | 7d | 89 ± 2 tested at 150 μM | 4.4 |
| 25 | 7e | 82 ± 9 | 24 ± 5 | 26 | 7f | 83 ± 3 | 7.7 ± 0.9 |
| 27 | 7g | 34 ± 6 | NA | 28 | 7h | 66 ± 3 | 7.5 ± 0.9 |
| 29 | 7i | 69 ± 3 | 15 ± 2 | 30 | 7l | 88.0 ± 0.09 | 1.91 ± 0.8 |
| 31 | 7m | 89 ± 1 | 1.31 ± 0.06 | 32 | 7n | 32 ± 3 | NA |
| 33 | 7o | 29 ± 6 | NA | 34 | 9a | 0 | NA |
| 35 | 9b | 0 | NA | 36 | 11 | 0 | NA |
| 37 | 13 | 47 ± 1 | NA | 38 | 14 | 85 ± 2 | 0.53 ± 0.05 |
| 39 | 15 | 0 | NA | | | | |

Compound Examples

Analytical thin layer chromatography (tlc or TLC) was carried out on silica gel plates (silica gel 60 F254). Eluted plates were visualized by exposure to ultraviolet light and then by staining with an ethanolic solution of phosphomolybdic acid. The products were isolated and purified using a flash chromatography system, with a mixture of hexanes and ethyl acetate as the eluent. The proton ($^1$H), $^{13}$C, HMBC and HSQC NMR spectra were taken on an 800 or a 500 MHz NMR spectrophotometer. Chemical shifts (δ) are expressed in ppm relative to chloroform or tetramethylsilane or dmso-proton NMR coupling constants (J) are expressed in Hz, and multiplicity is described as follows: s=singlet; d=doublet; t=triplet; q=quartet; ABq=AB quartet; quint=quintet; sext=sextet; sept=septet; br=broad; m=multiplet; dd=doublet of doublets; dt=doublet of triplets; dsept=doublet of septets; td=triplet of doublets; ddd=doublet of doublet of doublets. High-resolution mass spectra (HRMS) and electrospray (ESI) experiments were performed with a time-of-flight (TOF) mass detector. HPLC analysis was performed on Agilent 1100. Specific conditions used are indicated for each compound.

General Method for the Preparation of β-Ketoesters

A three necks-round bottom flask, equipped with addition funnel, nitrogen inlet and temperature probe was charged with anhydrous THF and NaH (60% dispersion in mineral oil, 2 equiv. c=1.25 M, concentration referred to moles of NaH). The suspension was stirred at room temperature for 10 min and then a THF solution of 2-acetylthiophene (25 mmol, 1 equiv. c=0.62 M) was added dropwise over a period of 20 min. A slight (4-5° C.) increase of the temperature was observed during the addition, and then the reaction mixture was warmed to 35° C. and stirred for 30 min. A THF solution of diethyl carbonate (50 mmol, 2 equiv., c=1.70 M) was added over a period of 1 hour. After one additional hour, the reaction mixture was cooled down to −10° C. and quenched with slow addition of water (5-10 ml), and then glacial acetic (3 ml) was added. The mixture was stirred for 20 min and then warmed to room temperature. The organic layer was separated and the aqueous layer was extracted with ethyl acetate (3×50 ml). The combined organic layers were washed with brine, dried with anhydrous $Na_2SO_4$ and concentrated under reduced pressure. Purification was done by automated flash chromatography using silica gel column and a mixture of hexanes and ethyl acetate as eluent. Hexanes (100%) was used to elute the excess of diethyl carbonate, and the amount of ethyl acetate was progressively increased from 20% to 50% to elute the title compound.

Ethyl 3-oxo-3-(thiophen-2-yl)propanoate (2a) (81% Yield)

Proton NMR (800 MHz, Chloroform-d) δ 7.75 (dd, J=3.7, 1.3 Hz, 1H), 7.70 (dd, J=4.9,1.3 Hz, 1H), 7.15 (dd, J=4.9, 3.7 Hz, 1H), 4.22 (q, J=7.1 Hz, 2H), 3.92 (s, 2H), 1.27 (t, J=7.1 Hz, 3H). $^{13}$C NMR (200 MHz, $CDCl_3$) δ 185.1, 167.1, 143.4, 135.1, 133.4, 128.5, 61.8, 46.7, 14.2.

Ethyl 3-oxo-3-(thiophen-3-yl)propanoate (2b) (89% Yield)

Proton NMR (500 MHz, Chloroform-d) δ 8.11 (dd, J=2.8, 1.3 Hz, 1H), 7.56 (dd, J=5.1, 1.3 Hz, 1H), 7.34 (dd, J=5.1, 2.8 Hz, 1H), 4.21 (q, J=7.1 Hz, 2H), 3.89 (s, 2H), 1.25 (d, J=7.1 Hz, 3H). $^{13}$C NMR (126 MHz, CDCl$_3$) δ 186.3, 167.2, 141.3, 133.3, 127.0, 126.7, 61.5, 47.2, 14.1. HRMS (ESI) Calcd for $C_9H_{11}O_3S^+$ 199.0423 found 199.0431.

Ethyl 3-oxo-3-(pyridin-2-yl)propanoate (2c) (58% Yield)

Proton NMR (500 MHz, Chloroform-d) δ 8.67 (ddd, J=4.8, 1.7, 0.9 Hz, 1H), 8.08 (dt, J=8.0, 1.1 Hz, 1H), 7.86 (td, J=7.7, 1.7 Hz, 1H), 7.49 (ddd, J=7.6, 4.7, 1.3 Hz, 1H), 4.20 (m, 4H), 1.24 (t, J=7.1 Hz, 3H). $^{13}$C NMR (126 MHz, CDCl3) δ 194.9, 168.5, 152.6, 149.2, 137.2, 127.7, 122.3, 61.4, 45.1, 14.3. HRMS (ESI) Calcd for $C_{10}H_{12}NO_3^+$ 194.0812 found 194.0809.

Ethyl 3-oxo-3-(pyridin-3-yl)propanoate (2d) (85% Yield)

This compound is a mixture of ketone and enol forms (2/1). Proton NMR (500 MHz, Chloroform-d) (ketone) δ 9.16 (dd, J=2.3, 0.9 Hz, 1H), 8.82 (dd, J=4.8, 1.7 Hz, 1H), 8.25 (ddd, J=8.0, 2.3, 1.7 Hz, 1H), 7.45 (ddd, J=8.0, 4.8, 0.9 Hz, 1H), 4.29 (q, J=7.1 Hz, 2H), 4.01 (s, 2H), 1.35 (t, J=7.1 Hz, 3H); (enol) δ 9.00 (dd, J=2.3, 0.9 Hz, 1H), 8.68 (dd, J=4.8, 1.7 Hz, 1H), 8.06 (ddd, J=8.0, 2.3, 1.7 Hz, 1H), 7.37 (ddd, J=8.0, 4.8, 0.9 Hz, 1H), 5.71 (s, 1H), 4.23 (q, J=7.2 Hz, 2H), 1.27 (t, J=7.1 Hz, 3H). $^{13}$C NMR (126 MHz, CDCl$_3$ list of carbons for both the ketone and the enol) δ 191.4, 173.0, 169.0, 167.0, 154.0, 151.8, 150.0, 147.4, 135.8, 133.4, 131.4, 129.4, 123.8, 123.4, 88.7, 61.8, 60.6, 46.0, 14.3, 14.1.

Ethyl 3-(4-chlorophenyl)-3-oxopropanoate (2e) 83% Yield

This compound is a mixture of ketone and enol forms (2/1). Proton NMR (500 MHz, CDCl$_3$) (ketone) δ 1.24 (t, J=7.0 Hz, 3H), 3.95 (s, 2H), 4.20 (q, J=7.0 Hz, 2H), 7.43 (d, J=7.0 Hz, 2H), 7.87 (d, J=7.0 Hz, 2H); (enol) δ 1.32 (t, J=7.5 Hz, 3H), 4.20 (q, J=7.5 Hz, 2H), 5.62 (s, 1H), 7.37 (d, J=7.0 Hz, 2H), 7.69 (d, J=7.0 Hz, 2H). $^{13}$C NMR (75 MHz, CDCl$_3$) (ketone) δ 13.0, 44.8, 60.4, 128.0, 128.9, 133.3, 139.1, 166.2, 190.3; (enol) δ 13.2, 59.4, 86.6, 126.3, 127.7, 130.8, 136.2, 168.9, 172.0.

Ethyl 3-(1-methyl-1H-pyrrol-3-yl)-3-oxopropanoate (2f) (62% Yield)

Proton NMR (500 MHz, Chloroform-d) δ 7.27 (m, 1H), 6.57 (dt, J=2.1, 1.2 Hz, 2H), 4.18 (q, J=7.1 Hz, 2H), 3.72 (s, 2H), 3.68 (s, 3H), 1.25 (t, J=7.1 Hz, 3H). $^{13}$C NMR (126 MHz, CDCl$_3$) δ 187.0, 168.2, 127.6, 125.2, 123.8, 110.0, 61.4, 47.2, 36.9, 14.3.

Ethyl 3-(2,5-dimethylthiophen-3-yl)-3-oxopropanoate (2g) (99% Yield)

Proton NMR (500 MHz, Chloroform-d) δ 6.93 (q, J=1.2 Hz, 1H), 4.20 (q, J=7.1 Hz, 2H), 3.79 (s, 2H), 2.66 (s, 3H), 2.39 (s, 3H), 1.26 (t, J=7.1 Hz, 3H). $^{13}$C NMR (126 MHz, CDCl3) δ 187.9, 167.6, 149.3, 135.5, 134.4, 125.9, 61.3, 48.7, 16.1, 15.0, 14.1.

General Method for the Preparation of Pyrazolones

Hydrazine monohydrate 64% (2.25 ml, 29.4 mmol, 1.05 equiv.) was added dropwise to a solution of the β-ketoester in absolute ethanol (28 mmol, c=0.19 M). The resulting orange solution was stirred under reflux for 3 hours. Conversion was checked by NMR, (few drops of the reaction mixture were dried under a stream of air and dissolved in CDCl$_3$) and upon disappearance of the starting material, the solvent was evaporated under reduced pressure and the resulting solid was triturated with acetone or ethanol.

5-(Thiophen-2-yl)-2,4-dihydro-3H-pyrazol-3-one (4a) (43% yield) triturated with acetone. Proton NMR (500 MHz, DMSO-d6) δ 12.06 (bs, 0.3H), 10.67 (bs, 0.7H), 9.66 (bs, 1H), 7.44 (bs, 1H), 7.32 (bs, 1H), 7.07 (bs, 1H), 5.68 (s, 1H proton at C-4).

5-(Thiophen-3-yl)-2,4-dihydro-3H-pyrazol-3-one (4b) (24% yield), triturated with ethanol. Proton NMR (500 MHz, DMSO-d6) δ 7.69 (d, J=1.8 Hz, 1H) 7.57 (dd, J=5.0, 2.9 Hz, 1H), 7.40 (dd, J=5.2, 1.3 Hz, 1H), 6.0 (bs, 1H), 5.73 (s, 2H). $^{13}$C NMR (126 MHz, DMSO) δ 160.9, 139.7, 132.4, 126.8, 125.5, 120.2, 86.7.

5-(Pyridin-2-yl)-2,4-dihydro-3H-pyrazol-3-one (4c) (54% yield), triturated with ethanol Proton NMR (500 MHz, DMSO-d6) δ 12.24 (bs, 1H), 9.70 (bs, 1H), 8.54 (d, J=4.8 Hz, 1H), 7.78 (m, 2H), 7.28 (m, 1H), 6.03 (s, 1H). $^{13}$C NMR (200 MHz, DMSO) δ 161.4, 149.2, 148.6, 142.5, 137.0, 122.7, 119.4, 88.1.

5-(Pyridin-3-yl)-2,4-dihydro-3H-pyrazol-3-one (4d) (81% yield), solid washed with ethanol after filtration. Proton NMR (500 MHz, DMSO-d6) δ 8.87 (dd, J=2.3, 0.9 Hz, 1H), 8.44 (dd, J=4.8, 1.6 Hz, 1H), 8.00 (ddd, J=8.0, 2.3, 1.6 Hz, 1H), 7.60 (bs, 2H), 7.38 (ddd, J=7.9, 4.8, 0.9 Hz, 1H), 5.86 (s, 1H). $^{13}$C NMR (126 MHz, DMSO) δ 161.1, 148.7, 146.4, 142.8, 132.2, 128.3, 124.2, 86.2.

5-(4-Chlorophenyl)-2,4-dihydro-3H-pyrazol-3-one (4e) (27% Yield), Triturated with Ethanol 5-(1-Methyl-1H-pyrrol-3-yl)-2,4-dihydro-3H-pyrazol-3-one (4f) (68% yield), triturated with ethanol. Proton NMR (500 MHz, DMSO-d6) δ 10.87 (s, 1H), 9.50 (s, 1H), 6.97 (dd, J=1.9, 1.9 Hz, 1H), 6.67 (dd, J=2.4, 2.4 Hz, 1H), 6.23 (dd, J=2.7, 1.7 Hz, 1H), 5.43 (s, 1H), 3.58 (s, 3H). $^{13}$C NMR (126 MHz, DMSO) δ 161.3, 139.5, 122.5, 118.9, 114.1, 105.6, 85.1, 35.7.

5-(2,5-Dimethylthiophen-3-yl)-2,4-dihydro-3H-pyrazol-3-one (4g) (32% yield), Proton NMR (500 MHz, DMSO-d6) δ 11.62 (s, 1H), 9.66 (s, 1H), 6.91 (d, J=1.3 Hz, 1H), 5.59 (s, 1H), 2.41 (s, 3H), 2.36 (s, 3H). $^{13}$C NMR (126 MHz, DMSO) δ 161.1, 138.4, 135.0, 131.8, 127.4, 125.2, 88.1, 14.7, 14.2.

2-Methyl-5-(thiophen-2-yl)-2,4-dihydro-3H-pyrazol-3-one (4h) (yield 51%), triturated with ethanol. Proton NMR (500 MHz, DMSO-d6) δ 11.08 (s, 1H), 7.34 (dd, J=5.0, 1.2 Hz, 1H), 7.24 (dd, J=3.5, 1.2 Hz, 1H), 7.00 (dd, J=5.1, 3.5 Hz, 1H), 5.66 (s, 1H), 3.50 (s, 3H). $^{13}$C NMR (126 MHz, DMSO) δ 152.9, 143.4, 137.8, 127.3, 124.1, 123.0, 83.1, 33.1.

General Method for the Preparation of 2,4-dihydropyrano[2,3-c]pyrazoles

Pyrazolone (12 mmol, 1.1 equiv.) was suspended in absolute ethanol (typical concentration c=0.3 mM) and malononitrile (1.1 equiv.), aldehyde (1 equiv.), and triethyl amine (0.11 equiv.) were added sequentially. The resulting suspension was stirred at room temperature (or at the temperature indicated) for 2 h, unless noted otherwise. Generally, the suspension clarified (due to the formation of polar intermediates), and as the reaction progressed, the product precipitated. The solid was isolated by filtration under vacuum and washed with cold ethanol.

6-Amino-4-(3-bromo-4-methoxyphenyl)-3-(thiophen-2-yl)-2,4-dihydropyrano [2,3-c]pyrazole-5-carbonitrile (6a)

The title compound was isolated as colorless solid in quantitative yield, starting from 3-bromo-4-methoxybenzaldehyde and 4a. Proton NMR (800 MHz, DMSO-d6) δ 13.03 (s, 1H), 7.58 (d, J=5.0 Hz, 1H), 7.27 (m, 2H), 7.13 (dd, J=8.5, 1.8 Hz, 1H), 7.06 (m, 1H), 7.02 (d, J=8.5 Hz, 1H), 6.98 (s, 2H), 4.79 (s, 1H), 3.80 (s, 3H). $^{13}$C NMR (200 MHz, DMSO) δ 159.9, 155.9, 154.1, 138.0, 133.0, 131.6, 129.5, 128.0, 127.6, 127.4, 125.9, 120.4, 112.6, 110.4, 96.8, 58.1, 56.1, 35.3. HRMS (ESI$^+$) Calcd for $C_{18}H_{14}BrN_4O_2S^+$ [M+H]$^+$ 429.0015 (100.0%), 430.9995 (97.3%), found 429.0070 and 431.0051.

6-Amino-4-(4-methoxyphenyl)-3-(thiophen-2-yl)-2,4-dihydropyrano [2,3-c]pyrazole-5-carbonitrile (6b)

The title compound was isolated as colorless solid in 64% yield, starting from 4-methoxybenzaldehyde and 4a. Proton NMR (800 MHz, DMSO-d6) δ 12.97 (s, 1H), 7.55 (dd, J=5.0, 1.2 Hz, 1H), 7.22 (dd, J=3.5, 1.3 Hz, 1H), 7.04 (m, 3H), 6.90 (m, 2H), 6.83 (m, 2H), 4.72 (s, 1H), 3.70 (s, 3H). $^{13}$C NMR (200 MHz, DMSO) δ 159.7, 158.0, 156.0, 136.4, 132.8, 129.8, 128.5, 127.5, 127.1, 125.5, 120.6, 113.7, 97.3, 58.7, 54.9, 35.8. HRMS (ESI$^+$) Calcd for $C_{18}H_{15}N_4O_2S+$ [M+H]$^+$ 351.0910 found 351.0920.

6-Amino-4-(3-bromophenyl)-3-(thiophen-2-yl)-2,4-dihydropyrano[2,3-c]pyrazole-5-carbonitrile (6c)

The title compound was isolated as colorless solid in 36% yield, starting from 3-bromobenzaldehyde and 4a. Proton NMR (800 MHz, DMSO-d6) δ 13.05 (s, 1H), 7.58 (m, 1H), 7.39 (ddd, J=8.0, 2.0, 1.0 Hz, 1H), 7.28 (t, J=1.9 Hz, 1H), 7.26 (m, 2H), 7.15 (d, J=7.7 Hz, 1H), 7.05 (m, 3H), 4.85 (s, 1H). $^{13}$C NMR (126 MHz, DMSO) δ 160.1, 155.8, 147.0, 133.0, 130.7, 130.0, 130.0, 129.4, 127.6, 127.4, 126.6, 125.9, 121.6, 120.3, 96.4, 57.6, 36.0. HRMS (ESI$^+$) Calcd for $C_{17}H_{12}BrN_4OS^+$[M+H]$^+$ 398.9910 found 398.9914.

6-Amino-4-(4-hydroxyphenyl)-3-(thiophen-2-yl)-2,4-dihydropyrano [2,3-c]pyrazole-5-carbonitrile (6d)

The title compound was isolated as colorless solid in 32% yield, starting from 4-hydroxybenzaldehyde and 4a. Proton NMR (800 MHz, DMSO-d6) δ 12.94 (s, 1H), 9.26 (s, 1H), 7.55 (dd, J=5.1, 1.1 Hz, 1H), 7.20 (dd, J=3.6, 1.2 Hz, 1H), 7.04 (dd, J=5.1, 3.6 Hz, 1H), 6.92 (m, 2H), 6.86 (s, 2H), 6.65 (m, 2H), 4.64 (s, 1H). $^{13}$C NMR (200 MHz, DMSO) δ 160.2, 156.5, 135.2, 133.3, 130.3, 128.9, 128.0, 127.6, 126.0, 121.1, 115.6, 98.0, 59.4, 49.1, 36.4. HRMS (ESI$^+$) Calcd for $C_{17}H_{13}N_4O_2S^+$ [M+H]$^+$ 337.0754 found 337.0785.

6-Amino-3-(thiophen-2-yl)-4-(p-tolyl)-2,4-dihydropyrano [2,3-c]pyrazole-5-carbonitrile (6e)

The title compound was isolated as colorless solid in 12% yield, starting from 4-methylbenzaldehyde and 4a. Proton NMR (500 MHz, DMSO-d6) δ 12.95 (s, 1H), 7.52 (d, J=5.0 Hz, 1H), 7.19 (d, J=3.6 Hz, 1H), 7.05 (d, J=7.8 Hz, 2H), 7.03-6.94 (m, 3H), 6.88 (s, 2H), 4.69 (s, 1H), 2.21 (s, 3H). $^{13}$C NMR (200 MHz, MeOD) δ 160.5, 156.4, 141.0, 136.4, 134.1, 129.6, 128.8, 127.3, 127.0, 126.4, 125.8, 120.3, 97.7, 59.1, 36.7, 19.7. HRMS (ESI$^+$) Calcd for $C_{18}H_{15}N_4OS^+$ [M+H]$^+$ 335.0961 found 335.0994.

6-Amino-4-(4-chlorophenyl)-3-(thiophen-2-yl)-2,4-dihydropyrano[2,3-c]pyrazole-5-carbonitrile (6f)

The title compound was isolated as colorless solid in 21% yield, starting from 4-chlorobenzaldehyde and 4a. Proton NMR (500 MHz, DMSO-d$_6$) δ 13.00 (s, 1H), 7.53 (dd, J=5.0, 1.2 Hz, 1H), 7.39-7.24 (m, 2H), 7.21 (dd, J=3.7, 1.2 Hz, 1H), 7.16-7.04 (m, 2H), 7.02 (dd, J=5.1, 3.6 Hz, 1H), 6.98 (s, 2H), 4.80 (s, 1H). $^{13}$C NMR (200 MHz, MeOD) δ 160.6, 156.2, 142.7, 134.2, 132.4, 129.3, 129.0, 128.2, 127.1, 126.6, 126.0, 120.1, 97.1, 58.3, 36.5. HRMS (ESI$^+$) Calcd for $C_{17}H_{12}ClN_4OS^+$ [M+H]$^+$ 355.0415 found 355.0414.

6-Amino-4-(4-nitrophenyl)-3-(thiophen-2-yl)-2,4-dihydropyrano[2,3-c]pyrazole-5-carbonitrile (6g)

The title compound was isolated as colorless solid in 8% yield, starting from 4-nitrobenzaldehyde and 4a. Proton NMR (500 MHz, DMSO-d$_6$) δ 13.08 (s, 1H), 8.24-8.04 (m, 2H), 7.52 (dd, J=5.0, 1.2 Hz, 1H), 7.47-7.33 (m, 2H), 7.24 (dd, J=3.7, 1.2 Hz, 1H), 7.10 (s, 2H), 7.02 (dd, J=5.1, 3.6 Hz, 1H), 5.01 (s, 1H). $^{13}$C NMR (200 MHz, MeOD) δ 160.9, 156.2, 151.2, 147.0, 134.3, 129.1, 128.6, 127.2, 126.7, 126.1, 123.4, 119.8, 96.5, 57.3, 36.8. HRMS (ESI$^+$) Calcd for $C_{17}H_{12}N_5O_3S^+$ [M+H]$^+$ 366.0655 found 366.06821.

6-amino-4-(9H-fluoren-3-yl)-3-(thiophen-2-yl)-2,4-dihydropyrano [2,3-c]pyrazole-5-carbonitrile (6h)

The title compound was isolated as colorless solid in 64% yield, starting from fluorene-2-carboxaldehyde and 4a. The reaction was run under reflux. Proton NMR (800 MHz, DMSO-d6) δ 13.01 (s, 1H), 7.84 (d, J=7.6 Hz, 1H), 7.80 (d, J=7.8 Hz, 1H), 7.54 (d, J=7.5 Hz, 1H), 7.51 (d, J=5.0 Hz, 1H), 7.36 (t, J=7.4 Hz, 1H), 7.31-7.27 (m, 2H), 7.27-7.21 (m, 2H), 7.02 (dd, J=5.0, 3.5 Hz, 1H), 6.97 (s, 2H), 4.87 (s, 1H), 3.88 (d, J=22.1 Hz, 1H), 3.83 (d, J=22.1 Hz, 1H). $^{13}$C NMR (200 MHz, DMSO) δ 160.4, 156.5, 143.8, 143.7, 143.5, 141.2, 140.4, 133.5, 130.2, 128.0, 127.7, 127.2, 127.1, 127.0, 126.2, 125.5, 124.4, 121.0, 120.3, 120.2, 97.8, 59.0, 37.2, 36.8. HRMS (ESI$^+$) Calcd for $C_{24}H_{17}N_4OS^+$ =409.1118, found 409.1121.

4-(1-Allylindolin-6-yl)-6-amino-3-(thiophen-2-yl)-2,4-dihydropyrano[2,3-c]pyrazole-5-carbonitrile (6i)

The title compound was isolated as a pale yellow solid in 34% yield, starting from 1-allyl-2,3-dihydro-1H-indole-5-carbaldehyde and 4a. The reaction was run at 60° C. for 3 h. Proton NMR (800 MHz, DMSO-d6) δ 12.92 (s, 1H), 7.56 (d, J=5.1 Hz, 1H), 7.24 (d, J=3.5 Hz, 1H), 7.05 (dd, J=5.1, 3.5 Hz, 1H), 6.83 (m, 3H), 6.72 (d, J=1.8 Hz, 1H), 6.42 (d, J=8.0 Hz, 1H), 5.86 (ddt, J=17.2, 10.2, 6.0 Hz, 1H), 5.27 (dq, J=17.2, 1.7 Hz, 1H), 5.17 (dq, J=10.2, 1.4 Hz, 1H), 4.60 (s, 1H), 3.66 (ddt, J=5.8, 4.3, 1.5 Hz, 2H), 3.24 (t, J=8.3 Hz, 2H), 2.80 (ddd, J=32.5, 15.7, 7.6 Hz, 2H). $^{13}$C NMR (200 MHz, DMSO-d6) δ 160.2, 156.5, 151.4, 134.8, 134.0, 133.2, 130.7, 130.4, 128.0, 127.6, 126.9, 125.9, 123.5, 121.2, 117.7, 107.0, 98.4, 59.8, 53.1, 51.8, 36.7, 28.3. HRMS (ESI$^+$) Calcd for $C_{22}H_{20}N_5OS^+$=402.1384, found 402.1386.

6-amino-4-(4-(benzyloxy)-3,5-dibromophenyl)-3-(thiophen-2-yl)-2,4-dihydropyrano[2,3-c]pyrazole-5-carbonitrile (6l)

The title compound was isolated as colorless solid in 69% yield, starting from 4-benzyloxy-3,5-dibromo-benzaldehyde and 4a. The reaction was run at 60° C. for 1 h. Proton NMR (800 MHz, DMSO-d6) δ 13.09 (s, 1H), 7.63 (dd, J=5.1, 1.2 Hz, 1H), 7.52 (m, 2H), 7.48-7.33 (m, 5H), 7.31 (dd, J=3.6, 1.2 Hz, 1H), 7.10 (m, 3H), 4.96 (s, 2H), 4.92 (s, 1H). $^{13}$C NMR (200 MHz, DMSO) δ 160.8, 156.2, 151.2, 144.1, 136.5, 133.6, 132.1, 129.7, 128.9, 128.8, 128.8 (overlapping), 128.7, 128.1, 128.1, 126.8, 120.7, 118.3, 96.6, 74.8, 57.5, 55.4, 35.6. HRMS (ESI$^+$) Calcd for $C_{24}H_{17}Br_2N_4O_2S^+$ =584.9414, found 584.9413.

6-Amino-4-(3-bromo-4-propoxyphenyl)-3-(thiophen-2-yl)-2,4-dihydropyrano [2,3-c]pyrazole-5-carbonitrile (6m)

The title compound was isolated as colorless solid in 64% yield, starting from 3-bromo-4-propoxybenzaldehyde and 4a. The reaction was run at 60° C. for 2 h. Proton NMR (800 MHz, DMSO-d6) δ 12.99 (s, 1H), 7.56 (dt, J=5.1, 1.0 Hz, 1H), 7.25 (m, 2H), 7.07 (dd, J=8.5, 2.2 Hz, 1H), 7.05 (ddd, J=4.7, 3.8, 0.8 Hz, 1H), 6.98 (d, J=8.5 Hz, 1H), 6.94 (s, 2H), 4.76 (s, 1H), 3.94 (t, J=6.3 Hz, 2H), 1.71 (dq, J=7.7, 6.6 Hz, 2H), 0.98 (td, J=7.4, 0.8 Hz, 3H). $^{13}$C NMR (200 MHz, DMSO-d6) δ 159.9, 155.8, 153.5, 137.9, 133.0, 131.5, 129.5, 127.9, 127.6, 127.3, 125.8, 120.3, 113.5, 110.8, 96.8, 70.0, 58.1, 35.3, 22.0, 10.4. HRMS (ESI$^+$) Calcd for $C_{20}H_{18}BrN_4O_2S^+$=457.0328, found 457.0328.

6-Amino-4-(3-bromo-4-(prop-2-yn-1-yloxy)phenyl)-3-(thiophen-2-yl)-2,4-dihydropyrano[2,3-c]pyrazole-5-carbonitrile (6n)

The title compound was isolated as off-white solid in 55% yield, starting from 3-bromo-4-(2-propyn-1-yloxy)benzaldehyde and 4a. The reaction was run at 60° C. for 1 h. Proton NMR (800 MHz, DMSO-d6) δ 13.02 (s, 1H), 7.58 (dd, J=5.1, 1.2 Hz, 1H), 7.29 (d, J=2.2 Hz, 1H), 7.26 (dd, J=3.6, 1.2 Hz, 1H), 7.13 (dd, J=8.6, 2.2 Hz, 1H), 7.09 (d, J=8.6 Hz, 1H), 7.06 (dd, J=5.1, 3.6 Hz, 1H), 6.98 (s, 2H), 4.86 (d, J=2.4 Hz, 2H), 4.80 (s, 1H), 3.59 (t, J=2.3 Hz, 1H). $^{13}$C NMR (200 MHz, DMSO-d6) δ 160.5, 156.3, 152.7, 139.3, 133.5, 132.2, 130.0, 128.3, 128.1, 127.8, 126.4, 120.9, 114.6, 111.3, 97.2, 79.3, 79.2, 58.5, 56.9, 35.8. HRMS (ESI$^+$) Calcd for $C_{20}H_{14}BrN_4O_2S^+$=453.0016, found 453.0013.

6-Amino-4-(2,3-dihydrobenzofuran-5-yl)-3-(thiophen-2-yl)-2,4-dihydropyrano [2,3-c]pyrazole-5-carbonitrile (6o)

The title compound was isolated as colorless solid in 60% yield, starting from 2,3-dihydrobenzofuran-5-carbaldehyde and 4a. The reaction was run at room temperature for 12 h. Proton NMR (800 MHz, DMSO-d6) δ 12.96 (s, 1H), 7.56 (dd, J=5.1, 1.2 Hz, 1H), 7.24 (dd, J=3.7, 1.2 Hz, 1H), 7.05 (dd, J=5.1, 3.6 Hz, 1H), 6.90 (m, 4H), 6.65 (d, J=8.1 Hz, 1H), 4.69 (s, 1H), 4.46 (m, 2H), 3.10 (m, 2H). $^{13}$C NMR (126 MHz, DMSO) δ 169.0, 159.8, 158.5, 156.0, 136.5, 132.8, 129.8, 127.5, 127.2, 125.6, 123.8, 120.6, 109.2, 108.3, 97.6, 70.9, 58.9, 36.1, 29.0. HRMS (ESI$^+$) Calcd for $C_{19}H_{15}N_4O_2S+[M+H]^+$ 363.0910 found 363.0941.

6-Amino-4-(4-azido-3-iodophenyl)-3-(thiophen-2-yl)-2,4-dihydropyrano[2,3-c]pyrazole-5-carbonitrile (6p)

The title compound was isolated as colorless solid in 24% yield, starting from 4-azido-3-iodobenzaldehyde and 4a. The reaction was run at room temperature for 12 h. Proton NMR (800 MHz, DMSO-d6) δ 13.04 (s, 1H), 7.59 (dd, J=5.1, 1.2 Hz, 1H), 7.56 (d, J=2.0 Hz, 1H), 7.28 (dd, J=3.6, 1.2 Hz, 1H), 7.25 (d, J=8.3 Hz, 1H), 7.22 (dd, J=8.3, 2.0 Hz, 1H), 7.07 (dd, J=5.0, 3.6 Hz, 1H), 7.02 (s, 2H), 4.83 (s, 1H). $^{13}$C NMR (200 MHz, DMSO) δ 160.0, 155.7, 142.8, 139.6, 138.2, 133.0, 129.3, 129.0, 127.6, 127.4, 126.0, 120.3, 119.4, 96.4, 57.6, 48.6, 35.2. HRMS (ESI$^+$) Calcd for $C_{17}H_{11}N_7OS^+$ [M+H]$^+$ 487.9785 found 487.9806.

6-Amino-4-(4-hydroxy-3-(trifluoromethyl)phenyl)-3-(thiophen-2-yl)-2,4-dihydropyrano[2,3-c]pyrazole-5-carbonitrile (6q)

The title compound was isolated as colorless solid in 14% yield, starting from 4-hydroxy-3-trifluoromethylbenzaldehyde and 4a. The reaction was run at room temperature for 12 h. Proton NMR (500 MHz, DMSO-d6) δ 12.97 (s, 1H) 10.42 (s, 1H), 7.54 (dd, J=5.1, 1.2 Hz, 1H), 7.22 (dt, J=4.9, 1.7 Hz, 2H), 7.15 (dd, J=8.5, 2.3 Hz, 1H), 7.02 (dd, J=5.1, 3.6 Hz, 1H), 6.94 (s, 2H), 6.89 (d, J=8.5 Hz, 1H), 4.79 (s, 1H). $^{13}$C NMR (126 MHz, DMSO) δ 159.9, 155.8, 154.5, 134.6, 133.0, 132.7, 129.4, 127.5, 127.3, 125.9, 125.3, 125.0, 120.4, 117.2, 114.81 (q, J=30.0, 29.5 Hz), 96.9, 58.0, 35.5. HRMS (ESI$^+$) Calcd for $C_{18}H_{12}F3N_4O_2S^+$ [M+H]$^+$ 405.0628 found 405.0626.

6-Amino-4-(5-isopropyl-4-methoxy-2-methylphenyl)-3-(thiophen-2-yl)-2,4-dihydropyrano[2,3-c]pyrazole-5-carbonitrile (6r)

The title compound was isolated as colorless solid in 71% yield, starting from 5-isopropyl-4-methoxy-2-methylbenzaldehyde and 4a. The reaction was run at 60° C. for 1 h. Proton NMR (800 MHz, DMSO-d6) δ 12.86 (s, 1H), 7.52 (d, J=4.9 Hz, 1H), 7.09 (d, J=3.4 Hz, 1H), 7.00 (dd, J=5.0, 3.6 Hz, 1H), 6.82 (s, 2H), 6.75 (s, 1H), 6.67 (s, 1H), 4.95 (s, 1H), 3.75 (s, 3H), 3.07 (hept, J=6.9 Hz, 1H), 2.28 (s, 3H), 1.05 (d, J=6.9 Hz, 3H), 0.97 (d, J=6.9 Hz, 3H). $^{13}$C NMR (200 MHz, DMSO) δ 160.4, 156.6, 155.2, 134.0, 133.9, 133.9 (overlapping), 133.6, 133.2, 130.3, 127.8, 127.7, 126.1, 121.1, 113.3, 98.1, 58.2, 55.7, 40.5, 26.4, 23.1, 22.9, 19.3. HRMS (ESI$^+$) Calcd for $C_{22}H_{23}N_4O_2S^+$=407.1537, found 407.1539.

6-Amino-4-(3-fluoro-4-methoxyphenyl)-3-(thiophen-2-yl)-2,4-dihydropyrano [2,3-c]pyrazole-5-carbonitrile (6s)

The title compound was isolated as colorless solid in quantitative yield, starting from 3-fluoro-4-methoxybenzaldehyde and 4a. Proton NMR (500 MHz, DMSO-d6) δ 12.98 (s, 1H), 7.55 (dd, J=5.0, 1.2 Hz, 1H), 7.24 (dd, J=3.6, 1.2 Hz, 1H), 7.08-7.01 (m, 2H), 6.98-6.87 (m, 4H), 4.76 (s, 1H), 3.77 (s, 3H). $^{13}$C NMR (126 MHz, DMSO) δ 159.9, 155.9, 151.1 (d, J=244.3 Hz), 145.8 (d, J=10.5 Hz), 137.3 (d, J=4.6 Hz), 133.0, 129.6, 127.6, 127.3, 125.8, 123.5, 120.4, 114.8 (d, J=18.0 Hz), 113.7, 96.7, 58.0, 35.6. HRMS (ESI$^+$) Calcd for $C_{18}H_{14}FN_4O_2S^+$=369.0816, found. 369.0811.

6-Amino-4-(3-chloro-4-methoxyphenyl)-3-(thiophen-2-yl)-2,4-dihydropyrano [2,3-c]pyrazole-5-carbonitrile (6t)

The title compound was isolated as colorless solid in 42% yield, starting from 3-chloro-4-methoxybenzaldehyde and 4a. The reaction was run under reflux. Proton NMR (800 MHz, DMSO-d6) δ 13.01 (s, 1H), 7.57 (d, J=5.0 Hz, 1H), 7.27 (d, J=3.6 Hz, 1H), 7.09 (m, 4H), 6.96 (s, 2H), 4.79 (s, 1H), 3.81 (s, 3H). $^{13}$C NMR (200 MHz, DMSO) δ 160.4, 156.3, 153.7, 138.1, 133.5, 130.0, 129.0, 128.1, 127.8, 127.8, 126.3, 121.2, 120.8, 113.2, 97.2, 58.6, 56.5, 35.9. HRMS (ESI$^+$) Calcd for $C_{18}H_{14}ClN_4O_2S^+$=385.0521, found 385.0543.

6-Amino-4-(3-iodo-4-methoxyphenyl)-3-(thiophen-2-yl)-2,4-dihydropyrano [2,3-c]pyrazole-5-carbonitrile (6u)

The title compound was isolated as colorless solid in 60% yield, starting from 3-iodo-4-methoxybenzaldehyde and 4a. The reaction was run at room temperature overnight. Proton NMR (800 MHz, DMSO-d6) δ 13.00 (s, 1H), 7.58 (dd, J=5.0, 1.2 Hz, 1H), 7.46 (d, J=2.2 Hz, 1H), 7.26 (dd, J=3.7, 1.2 Hz, 1H), 7.14 (dd, J=8.5, 2.2 Hz, 1H), 7.06 (dd, J=5.0, 3.7 Hz, 1H), 6.95 (s, 2H), 6.91 (d, J=8.5 Hz, 1H), 4.76 (s, 1H), 3.78 (s, 3H). $^{13}$C NMR (200 MHz, CDCl3) δ 159.9, 156.5, 155.8, 138.5, 137.6, 133.0, 129.5, 128.8, 127.6, 127.4, 125.8, 120.4, 111.4, 96.9, 86.0, 58.2, 56.3, 35.1. HRMS (ESI$^+$) Calcd for $C_{18}H_{14}IN_4O_2S^+$=476.9877, found 476.9860.

6-Amino-4-(4-hydroxy-3-(trifluoromethyl)phenyl)-3-(thiophen-2-yl)-2,4-dihydropyrano[2,3-c]pyrazole-5-carbonitrile (6v)

The title compound was isolated as colorless solid in 29% yield, starting from 4-methoxy-3-(trifluoromethyl)benzaldehyde and 4a. The reaction was run at 60° C. Proton NMR (500 MHz, DMSO-d6) δ 13.00 (s, 1H), 7.54 (dd, J=5.0, 1.2 Hz, 1H), 7.38-7.28 (m, 2H), 7.24 (dd, J=3.6, 1.2 Hz, 1H), 7.14 (d, J=8.6 Hz, 1H), 7.02 (dd, J=5.1, 3.6 Hz, 1H), 6.98 (s, 2H), 4.87 (s, 1H), 3.81 (s, 3H). $^{13}$C NMR (126 MHz, DMSO) δ 160.4, 156.3, 136.7, 133.5, 130.9, 129.8, 128.1, 127.9, 126.5, 125.9, 125.2, 123.1, 120.8, 116.9, 113.5, 97.1, 58.3, 56.5, 35.8. HRMS (ESI$^+$) Calcd for $C_{19}H_{14}F_3N_4O_2S^+$=419.0785, found 419.0789.

6-Amino-4-(3-bromo-4-methoxyphenyl)-3-(thiophen-3-yl)-2,4-dihydropyrano [2,3-c]pyrazole-5-carbonitrile (7a)

The title compound was isolated as colorless solid in 50% yield, starting from 3-bromo-4-methoxybenzaldehyde and 4b. The reaction was run at room temperature overnight. Proton NMR (500 MHz, DMSO-d6) δ 12.85 (s, 1H), 7.57 (m, 2H), 7.29 (m, 2H), 7.14 (dd, J=8.5, 2.2 Hz, 1H), 6.99 (d, J=8.5 Hz, 1H), 6.95 (m, 2H), 4.94 (s, 1H), 3.77 (s, 3H). $^{13}$C NMR (126 MHz, DMSO) δ 160.0, 155.7, 154.0, 138.4, 134.2, 131.4, 129.1, 127.8, 127.0, 125.5, 123.0, 120.5, 112.5, 110.3, 96.5, 58.0, 56.1, 35.1. HRMS (ESI$^+$) Calcd for $C_{18}H_{14}BrN_4O_2S^+$=429.0016, found 429.0009.

6-Amino-4-(3-iodo-4-methoxyphenyl)-3-(thiophen-3-yl)-2,4-dihydropyrano [2,3-c]pyrazole-5-carbonitrile (7b)

The title compound was isolated as colorless solid in 59% yield, starting from 3-iodo-4-methoxybenzaldehyde and 4b. The reaction was run at room temperature for 3 h. Proton NMR (500 MHz, DMSO-d6) δ 12.83 (s, 1H), 7.55 (m, 2H), 7.48 (d, J=2.2 Hz, 1H), 7.27 (dd, J=4.9, 1.5 Hz, 1H), 7.14 (dd, J=8.5, 2.2 Hz, 1H), 6.92 (s, 2H), 6.86 (d, J=8.5 Hz, 1H), 4.89 (s, 1H), 3.73 (s, 3H). $^{13}$C NMR (126 MHz, DMSO) δ 160.0, 156.3, 155.7, 138.8, 137.5, 134.2, 129.1, 128.7, 127.0, 125.5, 123.0, 120.5, 111.4, 96.6, 86.0, 58.1, 56.2, 34.9. HRMS (ESI$^+$) Calcd for $C_{18}H_{14}IN_4O_2S^+$=476.9877, found 476.9870.

6-Amino-4-(3-bromo-4-methoxyphenyl)-3-(pyridin-2-yl)-2,4-dihydropyrano [2,3-c]pyrazole-5-carbonitrile (7c)

The title compound was isolated as colorless solid in 86% yield, starting from 3-bromo-4-methoxybenzaldehyde and 4c. The reaction was run at room temperature overnight. Proton NMR (500 MHz, DMSO-d6) δ 13.20 (s, 1H), 8.54 (ddd, J=4.9, 1.9, 0.9 Hz, 1H), 7.75 (td, J=7.8, 1.8 Hz, 1H), 7.55 (dt, J=8.0, 1.1 Hz, 1H), 7.30 (d, J=2.2 Hz, 1H), 7.27 (ddd, J=7.6, 4.8, 1.0 Hz, 1H), 7.12 (dd, J=8.5, 2.2 Hz, 1H), 6.98 (s, 2H), 6.93 (d, J=8.6 Hz, 1H), 5.04 (s, 1H), 3.73 (s, 3H). $^{13}$C NMR (126 MHz, DMSO) δ 160.6, 156.30, 154.3, 149.8, 147.50, 139.1, 137.4, 132.1, 128.4, 125.36, 123.6, 121.0, 120.9, 112.8, 110.5, 99.4, 58.4, 56.5, 36.3. HRMS (ESI$^+$) Calcd for $C_{19}H_{15}BrN_5O_2^+$=424.0404 found 424.0401.

6-Amino-4-(3-iodo-4-methoxyphenyl)-3-(pyridin-2-yl)-2,4-dihydropyrano [2,3-c]pyrazole-5-carbonitrile (7d)

The title compound was isolated as colorless solid in 77% yield, starting from 3-iodo-4-methoxybenzaldehyde and 4c. The reaction was run at room temperature overnight. Proton NMR (500 MHz, DMSO-d6) δ 13.19 (s, 1H), 8.54 (ddd, J=4.9, 1.8, 0.9 Hz, 1H), 7.76 (td, J=7.8, 1.8 Hz, 1H), 7.57 (dt, J=8.1, 1.0 Hz, 1H), 7.52 (s, 1H), 7.29 (ddd, J=7.6, 4.8, 1.1 Hz, 1H), 7.16 (dd, J=8.5, 2.2 Hz, 1H), 6.99 (s, 2H), 6.84 (d, J=8.5 Hz, 1H), 5.03 (s, 1H), 3.72 (s, 3H). $^{13}$C NMR (126 MHz, DMSO) δ 160.2, 156.2, 155.8, 149.3, 147.0, 139.1, 137.8, 136.9, 128.8, 123.1, 120.6, 120.5, 111.2, 98.9, 85.6, 58.0, 56.2, 35.7. HRMS (ESI$^+$) Calcd for $C_{19}H_{15}IN_5O_2$=472.0265, found 472.0266.

6-Amino-4-(3-bromo-4-methoxyphenyl)-3-(pyridin-3-yl)-2,4-dihydropyrano [2,3-c]pyrazole-5-carbonitrile (7e)

The title compound was isolated as colorless solid in 38% yield, starting from 3-bromo-4-methoxybenzaldehyde and 4d. The reaction was run at room temperature. Proton NMR (500 MHz, DMSO-d$_6$) δ 13.10 (s, 1H), 8.65 (dd, J=2.4, 0.9 Hz, 1H), 8.47 (dd, J=4.8, 1.6 Hz, 1H), 7.87 (ddd, J=8.0, 2.4, 1.6 Hz, 1H), 7.37 (ddd, J=8.0, 4.8, 0.9 Hz, 1H), 7.27 (d, J=2.2 Hz, 1H), 7.08 (dd, J=8.5, 2.3 Hz, 1H), 7.00 (s, 2H), 6.94 (d, J=8.5 Hz, 1H), 5.09 (s, 1H), 3.75 (s, 3H). $^{13}$C NMR (126 MHz, DMSO) δ 160.0, 155.8, 154.0, 149.2, 147.0, 137.9, 135.3, 133.7, 131.6, 127.9, 124.6, 123.5, 120.4, 112.5, 110.2, 98.0, 57.8, 56.0, 35.1. HRMS (ESI$^+$) Calcd for $C_{19}H_{15}BrN_5O_2^+$=424.0404, found 424.0403.

6-Amino-4-(3-iodo-4-methoxyphenyl)-3-(pyridin-3-yl)-2,4-dihydropyrano [2,3-c]pyrazole-5-carbonitrile (7f)

The title compound was isolated as colorless solid in 5% yield, starting from 3-iodo-4-methoxybenzaldehyde and 4d.

The reaction was run at room temperature. Proton NMR (500 MHz, DMSO-d6) δ 13.09 (s, 1H), 8.62 (dd, J=2.4, 0.9 Hz, 1H), 8.45 (dd, J=4.8, 1.6 Hz, 1H), 7.84 (dt, J=8.0, 1.8 Hz, 1H), 7.43 (d, J=2.2 Hz, 1H), 7.34 (ddd, J=8.0, 4.9, 0.9 Hz, 1H), 7.07 (dd, J=8.5, 2.3 Hz, 1H), 6.96 (s, 2H), 6.81 (d, J=8.5 Hz, 1H), 5.03 (s, 1H), 3.70 (s, 3H). $^{13}$C NMR (126 MHz, DMSO) δ 160.0, 156.4, 155.8, 149.2, 147.1, 138.4, 137.6, 135.3, 133.7, 128.7, 124.6, 123.5, 120.4, 111.3, 98.2, 85.9, 57.9, 56.2, 35.0. HRMS (ESI$^+$) Calcd for $C_{19}H_{15}IN_5O_2^+$=472.0265, found 472.0265.

6-Amino-3-(4-chlorophenyl)-4-(3,4-dimethylphenyl)-2,4-dihydropyrano[2,3-c]pyrazole-5-carbonitrile (7g)

The title compound was isolated as colorless solid in 75% yield, starting from 3,4-dimethylbenzaldehyde and 4e. The reaction was run at room temperature. Proton NMR (800 MHz, DMSO-d6) δ 12.90 (s, 1H), 7.48 (m, 2H), 7.38 (m, 2H), 6.95 (d, J=8.3 Hz, 1H), 6.87 (s, 2H), 6.82 (d, J=6.4 Hz, 2H), 4.88 (s, 1H), 2.10 (s, 3H), 2.09 (s, 3H). $^{13}$C NMR (200 MHz, DMSO) δ 159.9, 156.0, 141.9, 136.6, 136.0, 134.4, 133.0, 129.3, 128.6, 128.2, 128.0, 127.5, 124.7, 120.5, 98.1, 58.4, 36.3, 19.4, 18.9. HRMS (ESI$^+$) Calcd for $C_{21}H_{18}ClN_4O^+$=377.1164, found 377.1164.

6-Amino-4-(3-bromo-4-methoxyphenyl)-3-(4-chlorophenyl)-2,4-dihydropyrano [2,3-c]pyrazole-5-carbonitrile (7h)

The title compound was isolated as colorless solid in 49% yield, starting from 3-bromo-4-methoxybenzaldehyde and 4e. The reaction was run at room temperature. Proton NMR (800 MHz, DMSO-d6) δ 12.96 (s, 1H), 7.50 (m, 2H), 7.39 (d, J=8.5 Hz, 2H), 7.23 (d, J=2.2 Hz, 1H), 7.08 (dd, J=8.5, 2.2 Hz, 1H), 6.94 (m, 3H), 5.01 (s, 1H), 3.75 (s, 3H). $^{13}$C NMR (200 MHz, DMSO) δ 160.0, 155.8, 154.0, 138.1, 136.9, 133.1, 131.5, 128.6, 128.1, 127.8, 127.3, 120.4, 112.4, 110.2, 97.6, 57.9, 56.1, 35.3. HRMS (ESI$^+$) Calcd for $C_{20}H_{15}BrClN_4O_2^+$=457.0062, found 457.0073.

6-Amino-3-(4-chlorophenyl)-4-(3-iodo-4-methoxyphenyl)-2,4-dihydropyrano [2,3-c]pyrazole-5-carbonitrilem (7i)

The title compound was isolated as colorless solid in 61% yield, starting from 3-iodo-4-methoxybenzaldehyde and 4e. The reaction was run at room temperature. Proton NMR (800 MHz, DMSO-d6) δ 12.98 (s, 1H), 7.51 (m, 2H), 7.41 (m, 2H), 7.25 (d, J=2.2 Hz, 1H), 7.09 (dd, J=8.5, 2.2 Hz, 1H), 6.96 (m, 3H), 5.03 (s, 1H), 3.76 (s, 3H). $^{13}$C NMR (200 MHz, DMSO) δ 160.0, 155.8, 154.0, 138.1, 136.9, 133.1, 131.5, 128.6, 128.1, 127.8, 127.3, 120.4, 112.4, 110.2, 97.6, 57.9, 56.1, 35.3. HRMS (ESI$^+$) Calcd for $C_{20}H_{15}ClIN_4O_2^+$=504.9923, found 504.9938.

6-Amino-4-(3-bromo-4-methoxyphenyl)-3-(1-methyl-1H-pyrrol-3-yl)-2,4-dihydropyrano[2,3-c]pyrazole-5-carbonitrile (7l)

The title compound was isolated as colorless solid in 96% yield, starting from 3-bromo-4-methoxybenzaldehyde and 4f. The reaction was run at room temperature. Proton NMR (500 MHz, DMSO-d6) δ 12.35 (s, 1H), 7.27 (d, J=2.1 Hz, 1H), 7.13 (dd, J=8.5, 2.1 Hz, 1H), 6.99 (d, J=8.6 Hz, 1H), 6.84 (s, 2H), 6.79 (d, J=1.9 Hz, 1H), 6.61 (t, J=2.4 Hz, 1H), 6.12 (dd, J=2.8, 1.7 Hz, 1H), 4.69 (s, 1H), 3.77 (s, 3H), 3.50 (s, 3H). $^{13}$C NMR (126 MHz, DMSO) δ 160.1, 155.6, 153.9, 138.8, 135.2, 131.5, 127.9, 122.6, 120.7, 120.2, 112.5, 111.7, 110.3, 105.9, 94.1, 58.2, 56.1, 35.8, 35.3. HRMS (ESI$^+$) Calcd for $C_{19}H_{17}BrN_5O_2^+$=426.0560, found 426.0555.

6-Amino-4-(3-iodo-4-methoxyphenyl)-3-(1-methyl-1H-pyrrol-3-yl)-2,4-dihydropyrano[2,3-c]pyrazole-5-carbonitrile (7m)

The title compound was isolated as colorless solid in 75% yield, starting from 3-iodo-4-methoxybenzaldehyde and 4f. The reaction was run at room temperature. Proton NMR (500 MHz, DMSO-d6) δ 12.34 (s, 1H), 7.48 (d, J=2.1 Hz, 1H), 7.14 (dd, J=8.5, 2.2 Hz, 1H), 6.88 (d, J=8.5 Hz, 1H), 6.84 (s, 2H), 6.79 (t, J=1.9 Hz, 1H), 6.61 (t, J=2.4 Hz, 1H), 6.12 (dd, J=2.7, 1.7 Hz, 1H), 4.65 (s, 1H), 3.75 (s, 3H), 3.51 (s, 3H). $^{13}$C NMR (126 MHz, DMSO) δ 160.1, 156.3, 155.6, 139.3, 137.5, 135.2, 128.7, 122.5, 120.7, 120.2, 111.7, 111.3, 105.9, 94.3, 85.9, 58.3, 56.3, 35.8, 35.2. HRMS (ESI$^+$) Calcd for $C_{19}H_{17}IN_5O_2^+$=474.0421, found 474.0424.

6-Amino-4-(3-bromo-4-methoxyphenyl)-3-(2,5-dimethylthiophen-3-yl)-2,4-dihydropyrano[2,3-c]pyrano-5-carbonitrile (7n)

The title compound was isolated as colorless solid in 49% yield, starting from 3-bromo-4-methoxybenzaldehyde and 4g. The reaction was run at room temperature. Proton NMR (500 MHz, DMSO-d6) δ 12.47 (s, 1H), 7.09 (d, J=2.0 Hz, 1H), 7.03-6.91 (m, 4H), 6.31 (d, J=1.4 Hz, 1H), 4.64 (s, 1H), 3.78 (s, 3H), 2.42-2.25 (m, 3H), 2.15 (s, 3H). $^{13}$C NMR (126 MHz, DMSO) δ 160.7, 154.7, 153.9, 138.2, 135.4, 135.2, 134.6, 131.6, 127.6, 126.4, 125.6, 120.6, 112.3, 110.1, 98.4, 56.9, 56.1, 35.3, 14.6, 13.4. HRMS (ESI$^+$) Calcd for $C_{20}H_{18}BrN_4O_2S^+$=457.0328, found 457.0329.

6-Amino-3-(2,5-dimethylthiophen-3-yl)-4-(3-iodo-4-methoxyphenyl)-2,4-dihydropyrano[2,3-c]pyrazole-5-carbonitrile (7o)

The title compound was isolated as colorless solid in 18% yield, starting from 3-iodo-4-methoxybenzaldehyde and 4g. The reaction was run at room temperature. Proton NMR (500 MHz, DMSO-d6) δ 12.43 (s, 1H), 7.27 (d, J=2.2 Hz, 1H), 7.00-6.92 (m, 3H), 6.81 (d, J=8.5 Hz, 1H), 6.29 (d, J=1.3 Hz, 1H), 4.59 (s, 1H), 3.73 (s, 3H), 2.28 (s, 3H), 2.12 (s, 3H). $^{13}$C NMR (126 MHz, DMSO) δ 160.7, 156.3, 154.7, 138.7, 137.7, 135.3, 135.2, 134.6, 128.4, 126.4, 125.6, 120.6, 111.2, 98.5, 85.5, 56.9, 56.3, 35.1, 14.7, 13.4. HRMS (ESI$^+$) Calcd for $C_{20}H_{18}IN_4O_2S^+$=505.0190, found 505.0181.

Ethyl 6-amino-4-(3-bromo-4-methoxyphenyl)-3-(thiophen-2-yl)-2,4-dihydropyrano[2,3-c]pyrazole-5-carboxylate (8)

Ethyl cyanoacetate (20.0 µl, 0.185 mmol) and triethyl amine (26.0 µl, 0.185 mmol) were added to a suspension of 3-Br-4-OMebenzaldehyde (38 mg, 0.176 mmol), in 2 ml of ethanol. The reaction was stirred at room temperature for 4 h (white suspension) and complete formation of the arylidene malononitrile was verified by tlc. Pyrazolone 4a was added and the reaction mixture was stirred at room temperature for 5 days. The precipitate was filtered under vacuum and the mother liquor was concentrated and purified by automated flash chromatography, using a 16 g silica gel column and a mixture of hexanes and ethyl acetate. The gradient was as follow: 10% ethyl acetate 3 min, 30% 10 min, 30% 15 min, 50% 20 min, 50% 30 min, 100% 33 min, 100% 43 min. The title compound was isolated in 15% yield as a colorless glassy solid. Proton $^1$H NMR (500 MHz, DMSO-d$_6$) δ 12.89 (s, 1H), 7.78 (s, 2H), 7.60 (dd, J=5.1, 1.2 Hz, 1H), 7.31 (dd, J=3.6, 1.2 Hz, 1H), 7.27 (d, J=2.2 Hz, 1H), 7.09 (dd, J=5.1, 3.6 Hz, 1H), 7.03 (dd, J=8.5, 2.2 Hz, 1H), 6.91 (d, J=8.6 Hz, 1H), 4.90 (s, 1H), 4.03 (dq, J=10.9, 7.1 Hz, 1H), 3.96 (dq, J=10.9, 7.1 Hz, 1H), 3.73 (s, 3H), 1.17 (t, J=7.1 Hz, 3H). $^{13}$C NMR (126 MHz, DMSO) δ 168.3, 161.0, 156.8, 153.4, 140.1, 132.3, 129.8, 128.2, 127.7, 127.2, 127.1, 125.3, 112.1, 109.4, 99.9, 77.5, 58.9, 56.0, 34.0, 14.2. HRMS (ESI$^+$) Calcd for C$_{20}$H$_{19}$BrN$_3$O$_4$S$^+$ [M+H]$^+$ 476.0274 (100%), 478.0254 (97%), found 476.0274 (100%), 478.0256 (97%).

6-Amino-4-(3-bromo-4-methoxyphenyl)-1-methyl-3-(thiophen-2-yl)-1,4-dihydropyrano[2,3-c]pyrazole-5-carbonitrile (9a)

The title compound was isolated as colorless solid in 64% yield, starting from 3-bromo-4-methoxybenzaldehyde and 4h. The reaction was run at room temperature for 3 h. Proton NMR (500 MHz, DMSO-d6) δ 7.34 (dd, J=4.9, 1.3 Hz, 1H), 7.33 (d, J=2.2 Hz, 1H), 7.19 (dd, J=8.5, 2.2 Hz, 1H), 7.12 (s, 2H), 7.00 (d, J=8.5 Hz, 1H), 6.89 (m, 2H), 4.85 (s, 1H), 3.78 (s, 3H), 3.73 (s, 3H). $^{13}$C NMR (126 MHz, DMSO) δ 158.5, 154.1, 145.6, 140.0, 137.7, 135.2, 131.6, 128.1, 127.5, 125.1, 124.7, 119.9, 112.4, 110.5, 94.2, 59.2, 56.1, 36.0, 34.0. HRMS (ESI$^+$) Calcd for C$_{19}$H$_{16}$BrN$_4$O$_2$S$^+$=443.0172, found 443.0171.

6-Amino-4-(3-iodo-4-methoxyphenyl)-1-methyl-3-(thiophen-2-yl)-1,4-dihydropyrano[2,3-c]pyrazole-5-carbonitrile (9b)

The title compound was isolated as colorless solid in 17% yield, starting from 3-iodo-4-methoxybenzaldehyde and 4h. The reaction was run at room temperature for 3 h. Proton NMR (500 MHz, DMSO-d6) δ 7.52 (d, J=2.2 Hz, 1H), 7.36 (dd, J=4.9, 1.3 Hz, 1H), 7.22 (dd, J=8.5, 2.2 Hz, 1H), 7.13 (s, 2H), 6.96-6.74 (m, 3H), 4.84 (s, 1H), 3.77 (s, 3H), 3.74 (s, 3H). $^{13}$C NMR (126 MHz, DMSO) δ 158.5, 156.5, 145.6, 140.0, 138.2, 137.6, 135.2, 129.0, 127.5, 125.1, 124.8, 120.0, 111.3, 94.3, 86.2, 59.3, 56.3, 35.8, 34.0. HRMS (ESI$^+$) Calcd for C$_{19}$H$_{16}$IN$_4$O$_2$S$^+$=491.0033, found 491.0026.

4-(3-Bromo-4-methoxyphenyl)-6-((ethoxymethyl)amino)-1-methyl-3-(thiophen-2-yl)-1,4-dihydropyrano[2,3-c]pyrazole-5-carbonitrile (11)

Compound 9a (50.0 mg, 0.11 mmol) was suspended in 0.80 ml of triethyl orthoformate and 0.20 ml of glacial acetic acid were added dropwise. The reaction mixture was heated to 110° C. in oil bath, in about 30 min and conversion was judged complete by tlc (R$_f$=0.45 using hexanes, ethyl acetate 1:1). The mixture was concentrated to dryness, and the crude was suspended in 1.00 ml of EtOH. Sodium borohydrate (6.4 mg, 0.17 mmol) was added and the reaction mixture was stirred at room temperature for 3 h. Upon complete conversion (monitored by tlc, R$_f$=0.30 using hexanes, ethyl acetate 1:1), the title compound was isolated by filtration under vacuum and washed first with ethyl ether and then with few drops of cold ethanol. The title compound was isolated as colorless solid in 62% yield. Proton NMR (500 MHz, DMSO-d6) δ 8.16 (t, J=6.6 Hz, 1H), 7.38 (dd, J=4.5, 1.8 Hz, 1H), 7.36 (d, J=2.2 Hz, 1H), 7.22 (dd, J=8.5, 2.2 Hz, 1H), 7.03 (d, J=8.5 Hz, 1H), 6.93 (m, 2H), 4.96 (s, 1H), 4.76 (dd, J=10.8, 6.9 Hz, 1H), 4.61 (dd, J=10.8, 6.3 Hz, 1H), 3.80 (s, 3H), 3.78 (s, 3H), 3.51 (qd, J=7.0, 4.5 Hz, 2H), 1.12 (t, J=7.0 Hz, 3H). $^{13}$C NMR (126 MHz, DMSO) δ 156.9, 154.3, 145.2, 140.1, 137.2, 135.0, 131.6, 128.1, 127.5, 125.2, 124.8, 119.1, 112.5, 110.6, 94.2, 71.4, 63.0, 62.5, 56.1, 36.2, 34.0, 15.0. HRMS (ESI$^+$) Calcd for C$_{22}$H$_{22}$BrN$_4$O$_3$S$^+$ =501.0591, found 501.0590.

4-(3-Bromo-4-methoxyphenyl)-6-(methylamino)-3-(thiophen-2-yl)-2,4-dihydropyrano[2,3-c]pyrazole-5-carbonitrile (13)

Compound 6a (105 mg, 0.244 mmol) was suspended in 1.60 ml of triethyl orthoformate and 0.40 ml of glacial acetic acid were added dropwise. The reaction vessel was immersed in in oil bath at 110° C., and the mixture was stirred for 40 min. Conversion was judged complete by tlc (R$_f$=0.45 using hexanes, ethyl acetate 1:1). The mixture was concentrated to dryness, and the crude was suspended in 10 ml of EtOH and cooled down in ice/water bath. Sodium borohydrate (23.0 mg, 0.610 mmol) was added in one portion and the reaction mixture was stirred for 15 min, then the ice/water bath was removed and the mixture was stirred for 1 h. Conversion was measured by TLC, using a mixture of hexanes, ethyl acetate 1:1, the product has R$_f$=0.30. Ethyl acetate (3 mL) was added and the mixture was concentrated under reduced pressure. The crude was dissolved with ethyl acetate (20 mL) and 20 ml of 0.5 M aqueous solution of acetic acid were added. The aqueous layer was extracted 3 times with 40 ml of ethyl acetate. The combined organic layers were dried with brine and anhydrous sodium sulfate. The crude was purified with automated flash chromatography, using a 16 g silica gel column and a mixture of hexane (A) and ethyl acetate (B) with the following gradient 3 min 0% B, 10 min 50% B, 18 min 50% B, 33 min 100% B, 43 min 100% B.

The title compound was isolated as colorless solid (62.0 mg), in 70% yield. Proton NMR (500 MHz, DMSO-d6) δ 13.07 (s, 1H), 7.55 (d, J=5.2 Hz, 1H), 7.26 (d, J=3.2 Hz, 1H), 7.24 (d, J=2.2 Hz, 1H), 7.10 (dd, J=8.5, 2.2 Hz, 1H), 7.07 (d, J=4.8 Hz, 1H), 7.03 (dd, J=5.0, 3.6 Hz, 1H), 6.99 (d, J=8.5 Hz, 1H), 4.77 (s, 1H), 3.77 (s, 3H), 2.82 (d, J=4.7 Hz, 3H). $^{13}$C NMR (126 MHz, DMSO) δ 159.5, 155.7, 154.1, 138.1, 133.0, 131.5, 129.5, 128.0, 127.6, 127.4, 125.8, 120.7, 112.5, 110.3, 96.8, 57.6, 56.1, 35.6, 28.1. HRMS (ESI$^+$) Calcd for C$_{19}$H$_{16}$BrN$_4$O$_2$S$^+$=443.0172, found 443.0143.

2-Acetyl-6-amino-4-(3-bromo-4-methoxyphenyl)-3-(thiophen-2-yl)-2,4-dihydropyrano[2,3-c]pyrazole-5-carbonitrile (14)

Compound 6a (50 mg, 0.11 mmol) was suspended in acetic anhydride (1 ml) and the mixture was stirred in a preheated oil bath at 110° C. for 30 min. Upon complete conversion (as judged by TLC with hexanes, ethyl acetate 1:1, R$_f$=0.48), the solvent was evaporated under reduced pressure, and the crude was purified by automated flash chromatography using a silica gel column (16 g) and a mixture of ethyl acetate (B) in hexanes (A), with the following gradient: 20 min 0 to 20% B, 70 min 24% B, 90 min 40% B. The title compound was isolated as a colorless solid in 73% yield. Proton NMR (500 MHz, DMSO-d6) δ 7.54 (dd, J=5.1, 1.1 Hz, 1H), 7.41 (d, J=2.2 Hz, 1H), 7.26 (d, J=2.2 Hz, 1H), 7.24 (d, J=2.2 Hz, 2H), 7.16 (dd, J=3.7, 1.1 Hz, 1H), 7.02 (d, J=8.6 Hz, 1H), 6.99 (dd, J=5.1, 3.7 Hz, 1H), 4.97 (s, 1H), 3.79 (s, 3H), 2.63 (s, 3H). $^{13}$C NMR (126 MHz, DMSO) δ 168.0, 158.3, 154.3, 147.5, 144.1, 137.0, 133.2, 131.7, 128.2, 127.9, 127.8, 127.5, 119.5, 112.5, 110.7, 98.2, 58.8, 56.1, 35.0, 23.1.

4-(3-Bromo-4-methoxyphenyl)-3-(thiophen-2-yl)-2, 4-dihydropyrano [2,3-c]pyrazole-5-carbonitrile (15)

Compound 6a (50 mg, 0.11 mmol) was dissolved in anhydrous DMF (1 mL) under N2 atmosphere and the resulting pale yellow solution was cooled down to −30° C. (internal temperature) in dry ice/acetone bath. Tert-butyl nitrite was added dropwise (30 μL, 0.25 mmol) (bright yellow solution after the addition), and the mixture was stirred for 1 h, while the temperature reached 0° C. The cold bath was then removed and the reaction was stirred for an additional hour at room temperature. Upon complete conversion (monitored by tlc and indicated by the disappearance of the spot corresponding to the starting material $R_f$=0.22 in hexanes, ethyl acetate 1:1). The reaction mixture was immersed in the cold bath and the internal temperature was reduced to −24° C. and then sodium borohydrate (13 mg, 0.35 mmol) was added in one portion, and the reaction mixture was stirred for one hour without controlling the temperature, then the cold bath was removed and the reaction was stirred at room temperature for 1 hour. Ethyl acetate (3 mL) was added, and the solvent was concentrated under reduced pressure. The crude was dissolved in ethyl acetate (5 mL), water (5 mL) was added and the pH was adjusted to 7 with saturated aqueous solution of NH$_4$Cl. The aqueous layer was extracted with ethyl acetate and the combined organic layers were treated with brine and anhydrous sodium sulfate. The crude was purified with automated flash chromatography using a 7 g silica gel column and a mixture of hexanes (A) and ethyl acetate (B) with the following gradient: 5 min 30% B, 10 min 55% B, 20 min 60% B. The title compound was isolated as a colorless solid in 31% yield. Proton NMR (500 MHz, DMSO-d6) δ 13.17 (s, 1H), 7.79 (d, J=1.1 Hz, 1H), 7.56 (d, J=5.1 Hz, 1H), 7.37 (d, J=2.2 Hz, 1H), 7.24 (d, J=3.5 Hz, 1H), 7.20 (dd, J=8.5, 2.2 Hz, 1H), 7.06-7.02 (m, 2H), 5.06 (d, J=1.1 Hz, 1H), 3.79 (s, 3H). $^{13}$C NMR (126 MHz, DMSO) δ 155.1, 154.6, 151.6, 135.4, 133.6, 132.3, 129.1, 128.8, 127.6, 127.6 (two peaks overlap, in fact the peak at 127.6 is higher than the others and similar compounds have two peaks with very close chemical shifts) 126.1, 117.3, 112.7, 110.6, 95.9, 94.2, 56.2, 35.7. HRMS (ESI$^+$) Calcd for C$_{18}$H$_{13}$BrN$_3$O$_2$S$^+$=413.9906 (100.0%), 415.9886 (97.3%) found 413.9901 (100.0%), 415.9879 (97.3%).

Those skilled in the art will recognize that numerous modifications can be made to the specific implementations described above. The implementations should not be limited to the particular limitations described. Other implementations may be possible.

It is intended that that the scope of the present methods and compositions be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

The invention claimed is:
1. A compound having a formula

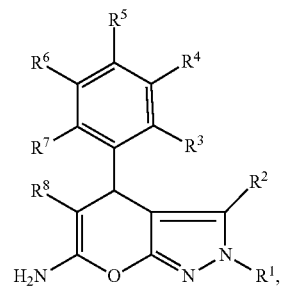

(I)

or a pharmaceutically acceptable salt thereof, wherein
R$^1$ is hydrogen, an alkyl or an acyl;
R$^2$ is an optionally substituted five-membered ring heterocycle;
R$^3$, R$^4$, R$^6$, and R$^7$ represent five substituents each independently selected from the group consisting of hydrogen, halo, azido, cyano, nitro, hydroxy, amino, thio, and derivatives thereof, and an acyl, alkyl, alkenyl, alkynyl, heteroalkyl, heteroalkenyl, oxyalkyl, heteroalkynyl, a heterocyclyl, cycloalkyl, cycloalkenyl, cycloheteroalkyl, cycloheteroalkenyl, aryl, arylalkyl, arylalkenyl, and arylalkynyl, each of which is optionally substituted; or any two adjacent substituents that are taken together with the attached carbons to form an optionally substituted heterocycle and each of other substituents is defined as above; one or more of R$^3$, R$^4$, R$^6$, and R$^7$ are not hydrogen;
R$^5$ is —OR, wherein R is an alkyl;
and
R$^8$ is cyano or a carboxy ester.
2. The compound according to claim 1, wherein R$^1$ is hydrogen, a C$_2$-C$_8$ acyl or a C$_2$-C$_8$ alkyl.
3. The compound according to claim 1, wherein R$^2$ is

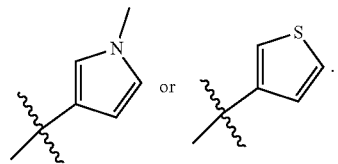

4. The compound according to claim 1, wherein R$^1$ is hydrogen, an acyl or an alkyl; and R$^2$ is

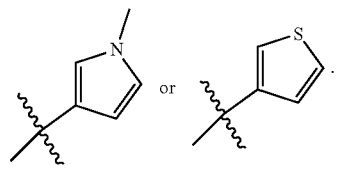

5. The compound according to claim 1, wherein R$^4$ or R$^6$ is an alkyl, halo, or haloalkyl.
6. The compound according to claim 1, wherein R$^5$ is —OCH$_3$.
7. The compound according to claim 1, wherein R$^5$ is —OCH$_3$; and R$^6$ is halo, alkyl, cyano, or haloalky.

8. The compound according to claim 1, wherein $R^4$ is hydrogen; $R^5$ is —$OCH_3$; and $R^6$ is halo, alkyl, cyano, or haloalky.

9. The compound according to claim 1, wherein $R^4$ is hydrogen; $R^5$ is —$OCH_3$; and $R^6$ is halo, alkyl, cyano, or haloalkyl.

10. The compound according to claim 1, wherein $R^1$ and $R^4$ are hydrogen; $R^5$ is —$OCH_3$; and $R^6$ is halo, alkyl, cyano, or haloalky.

11. The compound according to claim 1, wherein $R^4$ or $R^6$ is an alkyl, halo, or haloalkyl, and $R^5$ is —$OCH_3$.

12. The compound according to claim 1, wherein $R^8$ is a carboxy ester.

13. The compound according to claim 1, wherein said compound is

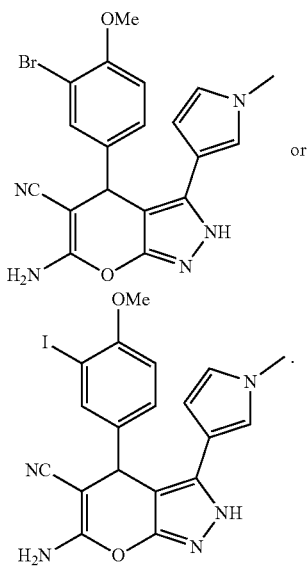

14. The compound according to claim 1, wherein said compound is

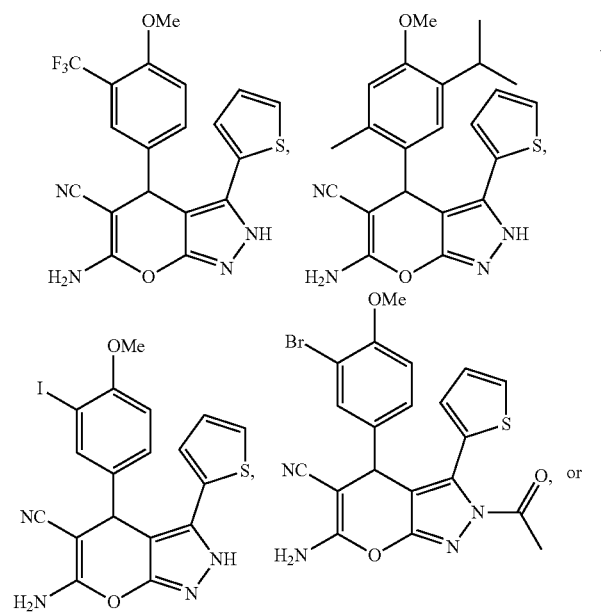

15. The compound according to claim 1, wherein said compound is

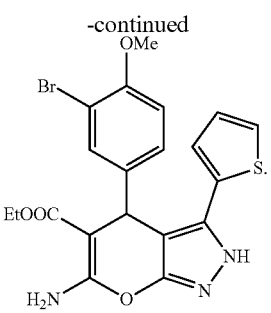

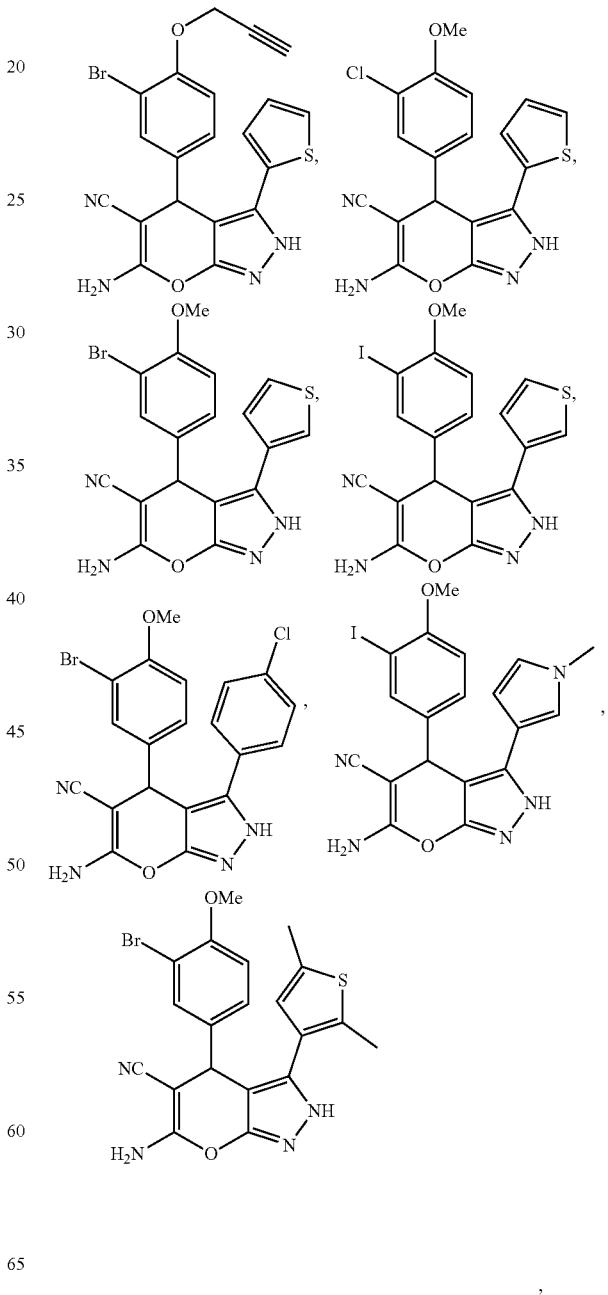

-continued

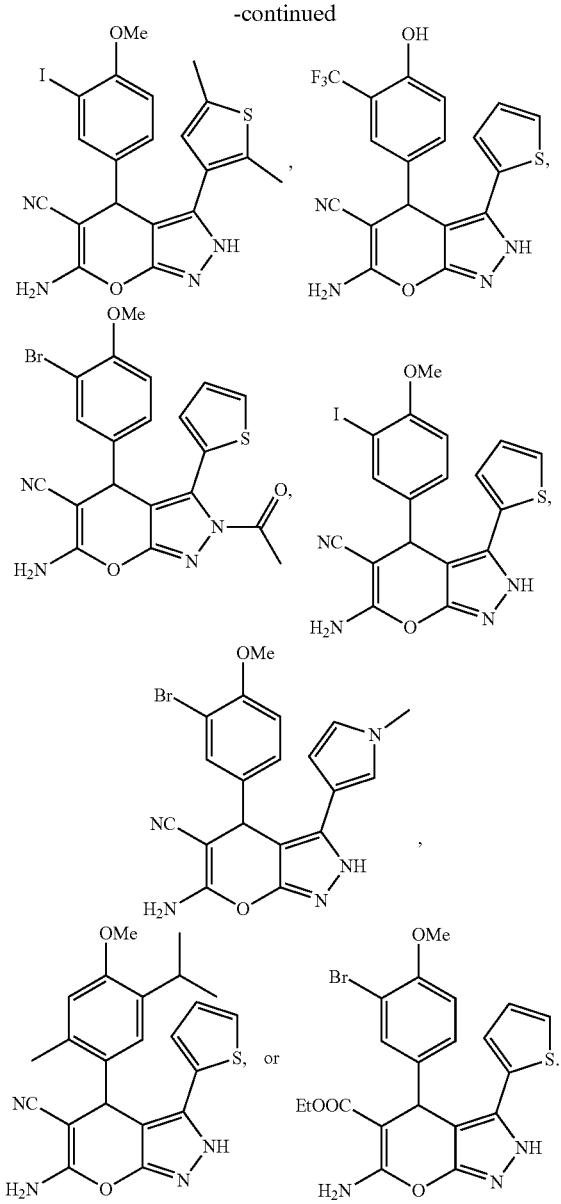

16. A pharmaceutical composition comprising one or more compounds having a formula

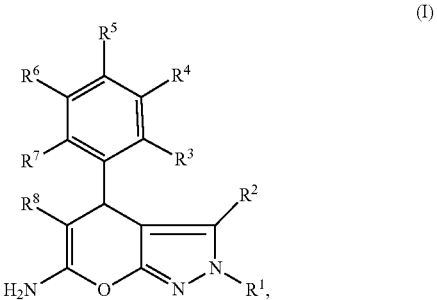

wherein $R^1$ is hydrogen, an alkyl or an acyl;

$R^2$ is an optionally substituted five-membered ring heterocycle;

$R^3$, $R^4$, $R^6$, and $R^7$ represent five substituents each independently selected from the group consisting of hydrogen, halo, azido, cyano, nitro, hydroxy, amino, thio, and derivatives thereof, and an acyl, alkyl, alkenyl, alkynyl, heteroalkyl, heteroalkenyl, oxyalkyl, heteroalkynyl, a heterocyclyl, cycloalkyl, cycloalkenyl, cycloheteroalkyl, cycloheteroalkenyl, aryl, arylalkyl, arylalkenyl, and arylalkynyl, each of which is optionally substituted; or any two adjacent substituents that are taken together with the attached carbons to form an optionally substituted heterocycle and each of other substituents is defined as above; one or more of $R^3$, $R^4$, $R^6$, and $R^7$ are not hydrogen;

$R^5$ is —OR, wherein R is an alkyl; and $R^8$ is cyano or a carboxy ester, or a pharmaceutically acceptable salt thereof, together with one or more diluents, excipients or carriers.

* * * * *